United States Patent
Brumfield et al.

(10) Patent No.: US 10,390,767 B2
(45) Date of Patent: Aug. 27, 2019

(54) HEMODYNAMIC RISK SEVERITY BASED UPON DETECTION AND QUANTIFICATION OF CARDIAC DYSRHYTHMIA BEHAVIOR USING A PULSE VOLUME WAVEFORM

(71) Applicant: Intelomed, Inc., Wexford, PA (US)

(72) Inventors: Anne M. Brumfield, Cranberry Township, PA (US); Jan K. Berkow, Allison Park, PA (US)

(73) Assignee: Intelomed Inc., Wexford, PA (US)

( * ) Notice: Subject to any disclaimer, the term of this patent is extended or adjusted under 35 U.S.C. 154(b) by 845 days.

(21) Appl. No.: 14/295,856

(22) Filed: Jun. 4, 2014

(65) Prior Publication Data

US 2014/0357995 A1 Dec. 4, 2014

Related U.S. Application Data

(60) Provisional application No. 61/830,821, filed on Jun. 4, 2013.

(51) Int. Cl.
*A61B 8/00* (2006.01)
*A61B 5/00* (2006.01)
(Continued)

(52) U.S. Cl.
CPC ........ *A61B 5/7282* (2013.01); *A61B 5/02416* (2013.01); *A61B 5/02108* (2013.01);
(Continued)

(58) Field of Classification Search
USPC ...................................................... 600/438
See application file for complete search history.

(56) References Cited

U.S. PATENT DOCUMENTS

| 4,450,527 A | 5/1984 | Sramek |
| 5,206,807 A | 4/1993 | Hatke et al. |

(Continued)

FOREIGN PATENT DOCUMENTS

| EP | 2392257 A2 | 12/2011 |
| EP | 1601287 B1 | 12/2012 |

(Continued)

OTHER PUBLICATIONS

Cruz et al., Algorithm Fusion for the Early Detection of Apnea-Bradycardia in Preterm Infants, Computers in Cardiology, (Sep. 17, 2006), 473-476 <http://ieeexplore.ieee.org/xpl/login.jsp?arnumber=4511891>.

(Continued)

*Primary Examiner* — Joel F Brutus
(74) *Attorney, Agent, or Firm* — Wood Herron & Evans LLP

(57) ABSTRACT

A method for identifying cardiac dysrhythmia behavior may include acquiring pulse volume wave data from a sensor associated with a patient, and calculating metrics associated with peaks detected therein. The metrics may include differences in amplitudes of successive pulse volume peaks and differences in the times of occurrence of successive pulse volume peaks. A dispersion analysis of the time differences, obtained during a defined time window, may result in one or more time difference dispersion metrics. Amplitude differences may be compared to an amplitude baseline, and time differences may be compared to a time baseline. Cardiac dysrhythmia behavior may be identified by a combination of an amplitude difference outside of the amplitude baseline, a corresponding time difference outside of the time baseline, and the values of one or more time difference dispersion metrics.

30 Claims, 22 Drawing Sheets

(51) Int. Cl.
*A61B 5/024* (2006.01)
*A61B 8/02* (2006.01)
*A61B 8/08* (2006.01)
*A61B 5/021* (2006.01)
*A61B 5/046* (2006.01)
*A61B 5/0464* (2006.01)

(52) U.S. Cl.
CPC .............. *A61B 5/046* (2013.01); *A61B 5/0464* (2013.01); *A61B 5/742* (2013.01); *A61B 8/02* (2013.01); *A61B 8/5223* (2013.01)

(56) References Cited

U.S. PATENT DOCUMENTS

| | | | |
|---|---|---|---|
| 5,292,339 | A | 3/1994 | Stephens et al. |
| 5,370,122 | A | 12/1994 | Kunig et al. |
| 5,810,011 | A | 9/1998 | Kunig |
| 5,830,131 | A | 11/1998 | Caro et al. |
| 5,860,918 | A | 1/1999 | Schradi et al. |
| 5,865,756 | A | 2/1999 | Peel, III |
| 5,900,433 | A | 5/1999 | Igo et al. |
| 6,112,115 | A | 8/2000 | Feldman et al. |
| 6,126,595 | A | 10/2000 | Amano et al. |
| 6,217,522 | B1 | 4/2001 | Shoshan |
| 6,270,461 | B1 | 8/2001 | Chio |
| 6,287,608 | B1 | 9/2001 | Levin et al. |
| 6,315,735 | B1 | 11/2001 | Joeken et al. |
| 6,334,849 | B1 | 1/2002 | Sunagawa |
| 6,339,716 | B1 | 1/2002 | Sawada et al. |
| 6,371,922 | B1 | 4/2002 | Baumann et al. |
| 6,485,431 | B1 | 11/2002 | Campbell |
| 6,575,912 | B1 | 6/2003 | Turcott |
| 6,719,705 | B2 | 4/2004 | Mills |
| 6,776,764 | B2 | 8/2004 | Pinsky |
| 6,858,006 | B2 | 2/2005 | MacCarter et al. |
| 7,044,918 | B2 | 5/2006 | Diab |
| 7,285,090 | B2 | 10/2007 | Stivoric et al. |
| 7,324,848 | B1 | 1/2008 | Turcott |
| 7,328,053 | B1 | 2/2008 | Diab et al. |
| 7,330,750 | B2 | 2/2008 | Erkkila et al. |
| 7,678,057 | B2 | 3/2010 | Berkow et al. |
| 7,794,406 | B2 | 9/2010 | Reisfeld et al. |
| 8,423,108 | B2 | 4/2013 | Berkow |
| 2001/0049476 | A1* | 12/2001 | Forstner ............ A61B 5/02225 600/494 |
| 2002/0045806 | A1 | 4/2002 | Baker et al. |
| 2003/0167010 | A1 | 9/2003 | Pinsky |
| 2004/0039273 | A1 | 2/2004 | Terry |
| 2005/0197675 | A1 | 9/2005 | David et al. |
| 2006/0167515 | A1 | 7/2006 | Stickney et al. |
| 2006/0293384 | A1 | 12/2006 | Whewell |
| 2007/0032732 | A1 | 2/2007 | Shelley et al. |
| 2007/0088222 | A1 | 4/2007 | Berkow et al. |
| 2007/0092632 | A1* | 4/2007 | Kubow ..................... A23J 3/08 426/656 |
| 2007/0123787 | A1 | 5/2007 | Kitajima et al. |
| 2007/0255146 | A1 | 11/2007 | Andrews et al. |
| 2008/0167564 | A1 | 7/2008 | Hete et al. |
| 2008/0228090 | A1 | 9/2008 | Wariar et al. |
| 2008/0255471 | A1 | 10/2008 | Naghavi et al. |
| 2008/0269625 | A1 | 10/2008 | Halperin et al. |
| 2008/0269626 | A1 | 10/2008 | Gallagher et al. |
| 2009/0093687 | A1* | 4/2009 | Telfort ................. A61B 5/0002 600/300 |
| 2009/0171227 | A1* | 7/2009 | Dziubinski .......... A61B 5/0452 600/516 |
| 2010/0081947 | A1 | 4/2010 | Suzuki |
| 2011/0046498 | A1* | 2/2011 | Klap .................... A61B 5/0205 600/534 |
| 2011/0245691 | A1 | 10/2011 | Silber |
| 2011/0282227 | A1 | 11/2011 | Zhang |
| 2012/0029373 | A1 | 2/2012 | Stadler et al. |
| 2012/0029374 | A1 | 2/2012 | Berkow |
| 2013/0080489 | A1 | 3/2013 | Ochs et al. |
| 2013/0267858 | A1 | 10/2013 | Berkow et al. |

FOREIGN PATENT DOCUMENTS

| | | | |
|---|---|---|---|
| EP | 2540222 | A2 | 1/2013 |
| WO | 0158517 | A2 | 8/2001 |
| WO | 03/077854 | A2 | 9/2003 |
| WO | 04/084720 | A2 | 10/2004 |
| WO | 2005/107584 | A1 | 11/2005 |
| WO | 2014/143962 | A2 | 9/2014 |

OTHER PUBLICATIONS

Feiseel et al., Respiratory Variation of Plethysmography Signal with a Pulse Oximeter: New Predictive Parameters of Fluid Responsiveness?, Proceedings of the American Thoracic Society, (Apr. 2006), 3:A295.

Kim et al., Can Cardiac Contractility be Estimated by an Inspiratory Hold Manueuver?, Proceedings of the American Thoracic Society, (Apr. 2006), 3:A296.

Kim et al., Determinates of Arterial Pulse Pressure and Stroke Volume Variation during Positive-Pressure Ventilation, Proceedings of the American Thoracic Society, (Apr. 2006), 3:A297.

Lamia et al., Brachial Pulse Pressure is Related to Total Arterial Compliance and Stroke Volume in ICU Patients: An Arterial Tonometric Study, Proceedings of the American Thoracic Society, (Apr. 2006), 3:A296.

Monnet et al., Measuring Aortic Diameter is Essential for Assessing Fluid Challenge by Esphageal Doppler, Proceedings of the American Thoracic Society, (Apr. 2006), 3:A296.

Pravisani et al., Short Term Prediction of Severe Bradycardia in Premature Newborns, Computers in Cardiology, (Sep. 21, 2003), 725-728.

Portet et al., Evaluation of On-Line Bradycardia Boundary Detectors from Neonatal Clinical Data, Conf IEEE Engl Med Biol Soc., (Aug. 22, 2007), 3288-3291.

Ridel et al., Prediction of Fluid Responsiveness in Spontaneously Breathing Patients: Response to Passive Leg Raising Measured by Pulse Contour Cardiac Output, Proceedings of the American Thoracic Society, (Apr. 2006), 3:A295.

Zamanian et al., Assessment of Cardiac Function and Ventilatory Efficiency by Noninvasive $CO_2$ Monitoring during Reduction of Ventilatory Support in Patients with CHF, Proceedings of the American Thoracic Society, (Apr. 2006), 3:A296.

International Search Report for PCT/US2014/040890 dated Nov. 4, 2014.

International Search Report for PCT/US2014/042012 dated Nov. 10, 2014.

International Search Report for PCT/US2014/050771 dated Dec. 1, 2014.

Lown et al., "Approaches to Sudden Death from Cornonary Heart Disease", Circulation, vol. 44, No. 1, Jul. 1, 1971, 14 pages.

European Patent Office, Supplementary Search Report issued in EP 14807798.5 dated Jan. 9, 2017, 10 pages.

* cited by examiner

HEMODYNAMIC RISK SEVERITY BASED UPON DETECTION AND QUANTIFICATION OF CARDIAC DYSRHYTHMIA BEHAVIOR USING A PULSE VOLUME WAVEFORM

CLAIM OF PRIORITY

This application claims priority to and benefit of U.S. Provisional Application Ser. No. 61/830,821 filed Jun. 4, 2013 entitled "Detection and Quantification of Cardiac Dysrhythmia Behavior Using a Pulse Volume Waveform," the disclosure of which is incorporated herein by reference in its entirety.

BACKGROUND

Cardiac electrophysiology refers to the orchestration of electrical pulses that cause the myocardium to contract in a coordinated manner to efficiently pump blood into the arterial tree. Suboptimal physiological alterations that effect the cardiac myocyte milieu can compromise the myocyte function and adversely affect the electrical conduction tissue. As a result, the electrical pulse sequences of the heart may be altered leading to abnormal cardiac sinus rhythms thereby causing dysynchronous or suboptimal myocardial contractile behaviors.

The electrical pulse sequences of the heart may be monitored using an electrocardiography (ECG) device. An ECG device may use multiple electrodes placed across the thorax to obtain millivolt level electrical changes associated with the depolarization of the myocardium and subsequent contraction of the myocardial cells. Typical ECG patterns representing sequences of myocardial repolarization/depolarization events may be referred to as a PQRST ECG tracing.

Contractile abnormalities, as observed in ECG traces, can be characterized as irregular heartbeats or arrhythmias that may manifest as tachycardia, bradycardia, palpitations, or fibrillation. Practitioners having domain expertise in electrocardiology may be able to differentiate abnormal ECG patterns from normal ECG patterns. Practitioners may also be adept at recognizing specific types of arrhythmias via PQRST ECG tracing patterns or behaviors. These ECG patterns provide clues as to the nature or cause of the arrhythmia for purposes enabling treatment that may be part of cardiac health management. For example, arrhythmias can be used to identify numerous forms of physiological dysfunction that include thryroid dysfunction, anemia, myocardial ischemic conditions, and multiple electrical pathways that result in poor cardiac function. In these examples, the recognition of an arrhythmia serves as part of a patient assessment to either diagnose a pathology, thereby enabling its treatment, or top predict onset of a pathology, thereby enabling overall patient management.

Alternatively, cardiac arrhythmias can result from myocardial ischemic conditions and result in decreased cardiac output. Decreased cardiac output may contribute to a hemodynamically unstable physiological state and predispose a patient to life threatening conditions. Therefore, a second purpose of arrhythmia detection may be to serve as part of a real-time hemodynamic monitoring tool. Integral to facilitating this clinical utility can be the ability to characterize the dysrhythmia behavior in terms of the severity of its adverse effect on cardiovascular hemodynamics. Use of physiological feedback of dysfunctional cardiac behavior in concert with other hemodynamic parameters can provide valuable information to characterize the overall physiologic behavior or state of a patient. Measures related to severity of cardiac related hemodynamic instability measures can provide valuable real-time feedback as a part of a hemodynamic monitor to manage patient stability and/or determine appropriate intervention for this purpose.

The pulse waveform obtained from a pulse oximeter, also referred to as a photoplethysmograph, is a mature technology that can be used as a standalone monitor or readily integrated as part of a hemodynamic monitoring system. The photoplethysmograph is not capable of capturing electrophysiology signals. However, patterns based upon temporal alterations of the pulse waveform features can be used to recognize the severity of the adverse hemodynamic impact that the cardiac dysfunction exibits based upon the degree of specific waveform feature abnormality and frequency of incidence. The resultant clinical utility may be to provide either a standalone or component of a hemodynamic monitoring device that enables real-time feedback as a hemodynamic instability monitor based upon pre-identified photoplethysmograph pulse waveform features.

SUMMARY

In an embodiment, a method for identifying a cardiac dysrhythmia behavior may include receiving, by a computing device, a biological signal emulating an arterial pulse wave from a sensor in data communication with a human body, identifying, by the computing device, a plurality of signal peaks within the biological signal, identifying, by the computing device, a peak amplitude for each of the plurality of signal peaks, identifying, by the computing device, a time occurrence for each of the plurality of signal peaks, calculating, by the computing device, a plurality of amplitude differences, in which each amplitude difference of the plurality of amplitude differences is calculated from a first peak amplitude of a first peak and a second peak amplitude of a second peak, calculating, by the computing device, a plurality of time differences, in which each time difference of the plurality of time differences is calculated from a first time occurrence of the first peak and a second time occurrence of the second peak, calculating, by the computing device, at least one time difference dispersion metric from the plurality of time differences, and identifying, by the computing device, a cardiac dysrhythmia behavior of the biological signal from the at least one time difference dispersion metric, if at least one anomalous amplitude difference calculated from a first anomalous peak and a second anomalous peak exceeds an amplitude threshold and at least one anomalous time difference calculated from the first anomalous peak and the second anomalous peak exceeds a time threshold.

DETAILED DESCRIPTION

Figure 1A:
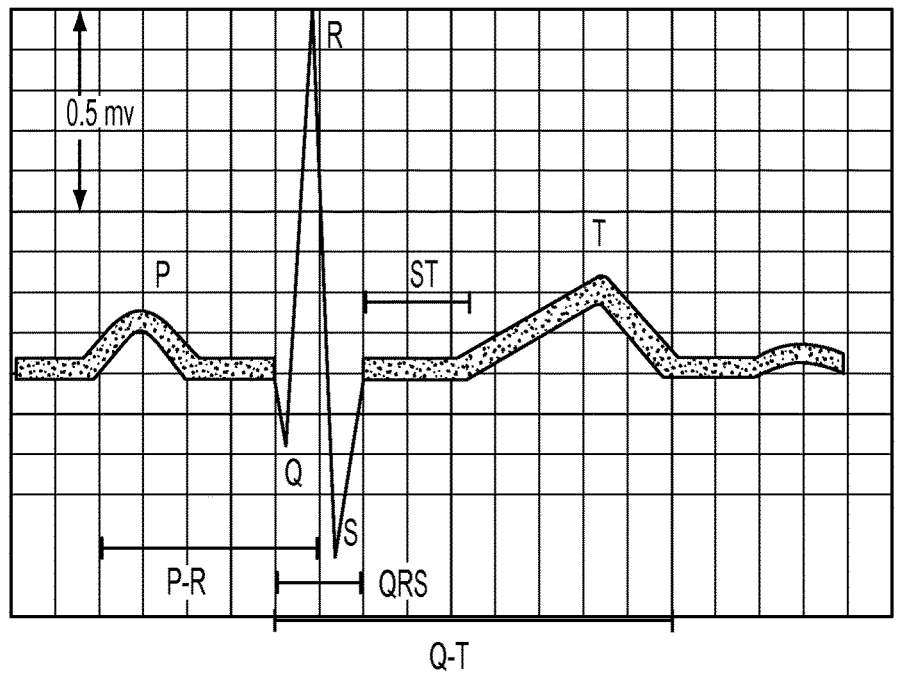
FIG. 1A depicts a normal human ECG tracing in accordance with some embodiments.

As disclosed above, transient or prolonged myocardial ischemia may be one of the frequent causes of arrhythmias. In some instances, myocardial ischemia, and the concomitant arrhythmias, may result from hypovolemic shock such as induced during hemodialysis. Additionally, segmental myocardial ischemia during hemodialysis may result in left ventricular regional wall motion abnormalities manifested by inconsistent left ventricular contractility patterns. While an ECG trace may be used by a health care provider to monitor and diagnose the specific electrocardio-behavior responsible for specific arrhythmias, such a device may not provide information regarding anomalies in the hemodynamics of patient blood-flow.

A pulse oximeter is a sensor capable of detecting the pulsatile flow of blood through the vasculature and producing a pulse waveform that can emulate an arterial pulse wave from a patient. Such a sensor can be used as a standalone monitoring device or may be readily integrated in a hemodynamic monitoring system. One non-limiting example of a pulse oximeter may include a photoplethysmograph. The pulse oximeter may not be capable of capturing cardiac electrophysiology signals. However, cardiac dysrhythmia may be deduced from alterations in normal pulse waveform patterns due to the effects of cardiac dysrhythmia on blood flow. The severity of the impact of such cardiac dysrhythmia on patient hemodynamic functions may be characterized by anomalous features in the pulse waveform patterns. In some non-limiting examples, the impact of cardiac dysrhythmia on hemodynamic functions may be characterized by specific anomalous pulse waveform features and the frequency of their occurrence. Methods of analyzing pulse volume waveform features derived from pulse oximeters (or similar devices) may be used by a health care provider to monitor hemodynamic instability in a patient, for example during a therapeutic procedure. Such methods may be embodied either in a standalone device or as a non-limiting component of a hemodynamic monitoring system.

Disclosed below are embodiments of a real-time method to detect and quantify specific types of cardiac dysrhythmias by applying an algorithm-based "toolkit" to a pulse waveform captured from a photo-plethysmograph (PPG) or other source producing a pulse volume waveform. The toolkit may include functions to assess changes in one or more features of a patient's pulse volume waveform morphology to identify specific dysrhythmia patterns typically recognized using an ECG trace. Non-limiting examples of pulse waveform features may include a pulse amplitude and an inter-pulse occurrence time. In some embodiments, such features may be compared to one or more of such features maintained in one or more feature databases. In one non-limiting example, a feature database may be derived from data obtained from a population of patients demonstrating such features. In another non-limiting example, a feature database may be derived from one or more animal models. In yet another non-limiting example, a feature database may be derived from data obtained from the same patient over time. In still another non-limiting example, a feature database may be derived from one or more mathematical models.

Some non-limiting examples of dysrhythmias potentially characterizable by the disclosed method may include supraventricular arrhythmia, ventricular arrhythmia, and bradyarrhythmia. Examples of supraventricular arrhythmias may include, without limitation, premature atrial contraction, paroxysmal supraventricular tachycardia, bypass tract tachycardia, AV nodal reentrant tachycardia, atrial tachycardia, atrial flutter, and atrial fibrillation. Examples of ventricular arrhythmias may include, without limitation, premature ventricular contraction, ventricular tachycardia, ventricular fibrillation, and long QT syndrome. Some ventricular arrhythmias may include multi-geminal premature ventricular contraction, such as bigeminal premature ventricular contraction, trigeminal premature ventricular contraction, or quadrigeminal premature ventricular contraction. Bradyarrhythmias may include sinus node dysfunction and heart block.

FIGS. 1A through 1D illustrate various ECG trace patterns.

FIG. 1A depicts a typical normal human ECG trace, illustrating features often used by health care providers to assess the nature of cardiac contractility. The ECG trace is frequently described in terms of the PQRST features, as indicated in FIG. 1A. The P feature generally corresponds to the depolarization of the atria of the heart, and is typically initiated at the sinoatrial node. The QRS complex typically corresponds to the ventricular depolarization, and typically is initiated at the atrioventricular node. The P-R time interval generally represents an electrical conduction time lag between the onset of atrial contraction and the onset of ventricular contraction. The Q-R time interval generally is the total time required for complete ventricular electrical depolarization and hence ventricular contraction. The T feature corresponds to the repolarization of the ventricular tissue, and the S-T interval is a lag time between ventricular depolarization and the onset of ventricular re-polarization. Other features may be found in an abnormal ECG depending on the pathology. Not shown in FIG. 1A is an R-R interval that generally corresponds to the time between successive ventricular contractions. For a normally functioning heart, the R-R interval is related to the heart rate.

Figure 1B:
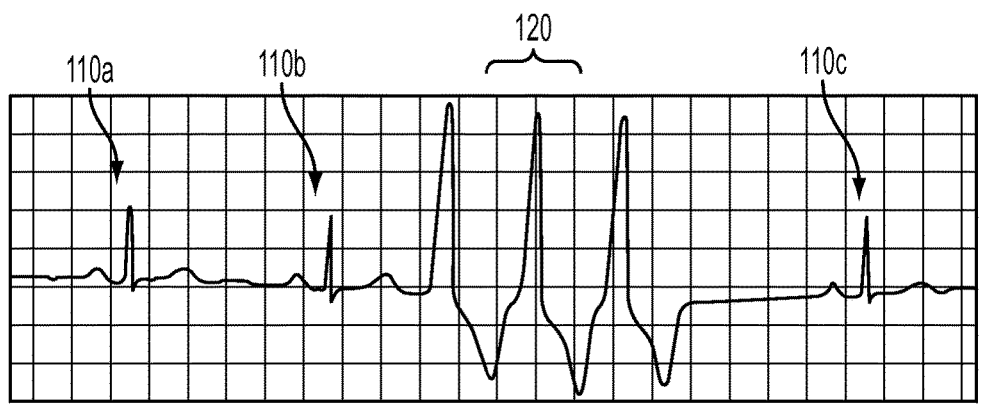
FIG. 1B depicts a human ECG tracing illustrating premature ventricular contractions in accordance with some embodiments.

FIG. 1B illustrates an ECG trace of a premature ventricular contraction (PVC) cardiac event. In FIG. 1B, three normal PQRST features (110a,b,c) may be observed. In addition, a group of sequential ventricular depolarizations 120 are illustrated. It may be noted that the ventricular contractions may be considered a group of QRS complexes without either a leading P wave (indicating atrial contraction) or following T wave (indicating complete ventricular repolarization). In FIG. 1B, three such sequential ventricular depolarizations 120 are depicted, a condition typically termed ventricular tachycardia.

Figure 1C:
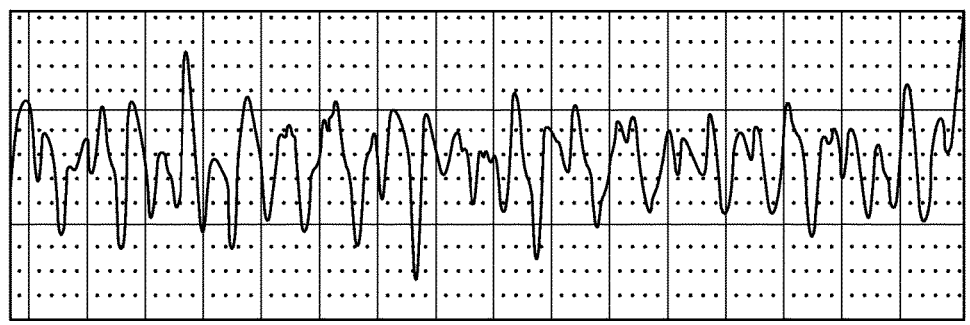
FIG. 1C depicts a human ECG tracing illustrating ventricular fibrillation in accordance with some embodiments.

FIG. 1C illustrates an ECG trace resulting from ventricular fibrillation. In FIG. 1C, no normal PQRST features may be observed, and the ECG trace indicates that the ventricular tissue rapidly depolarizes without any observable rhythm.

Figure 1D:
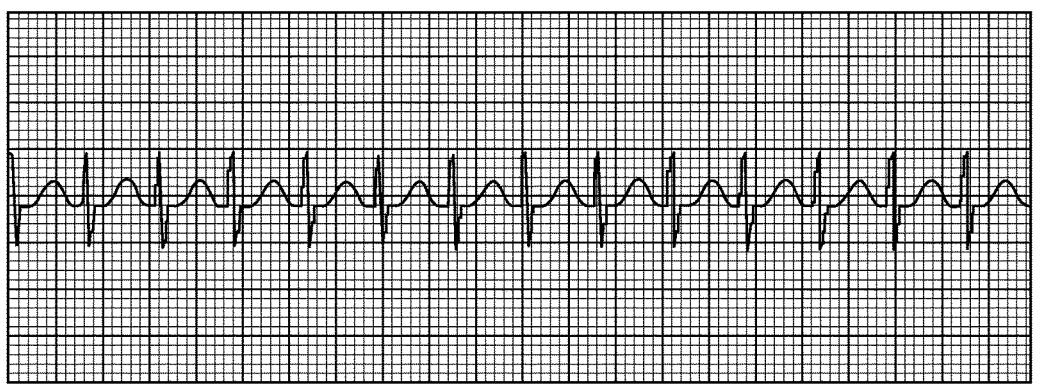
FIG. 1D depicts a human ECG tracing illustrating supraventricular tachycardia in accordance with some embodiments.

FIG. 1D illustrates an ECG trace related to supraventricular tachycardia. In some instances, a generally normal but narrowed QRS feature may be observed and the R-R interval may be decreased. In FIG. 1D, the P wave and T wave may be merged. In some cases, the supraventricular tachycardia may be caused by a re-entrant stimulation at the sinoatrial node. FIG. 1D may depict such a sinoatrial re-entrant tachycardia.

Figure 2A:
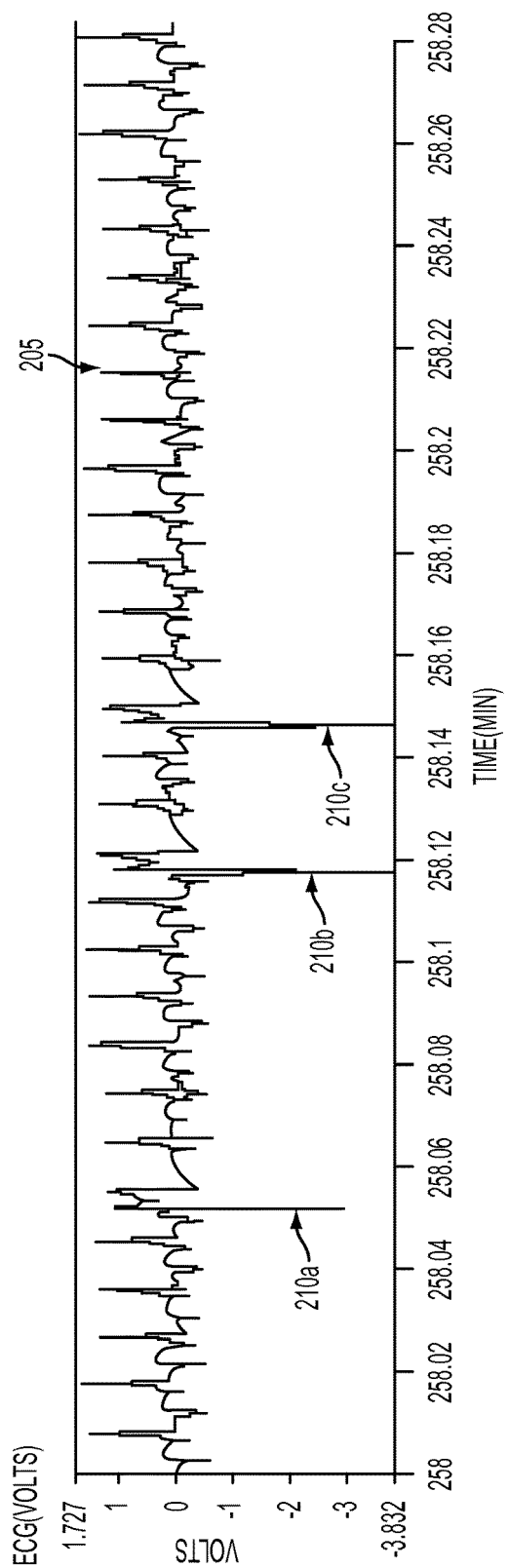
FIGS. 2A and 2B depict a porcine ECG tracing and corresponding pulse volume waveform, respectively, in accordance with some embodiments.
Figure 2B:
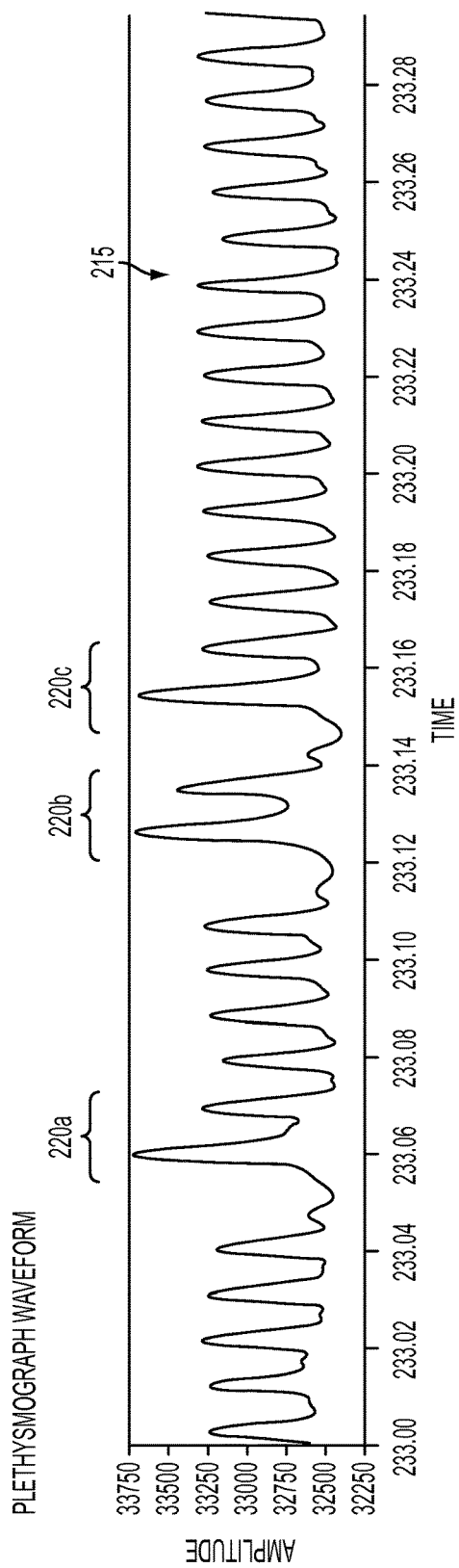

FIGS. 2A and 2B illustrate a porcine ECG tracing and corresponding pulse volume waveforms (for example, from a plethysmograph), respectively. The ECG tracing in FIG. 2A illustrates number of normal ECG waveforms 205 along with three abnormal ECG waveforms (210a, 210b, and 210c). The corresponding pulse volume waveforms in FIG. 2B illustrates normal pulse volume waveforms 215 along with three abnormal pulse volume waveforms (220a, 220b, and 220c). The structure of the abnormal pulse volume waveforms (220a, 220b, and 220c) may demonstrate premature ventricular contractions that may be manifested as ectopic or missed beats. It may be appreciated that at least some abnormal ECG waveforms (210a, 210b, and 210c) may present equivalent abnormal pulse volume waveforms (220a, 220b, and 220c) in the pulse volume trace.

Figure 2C:
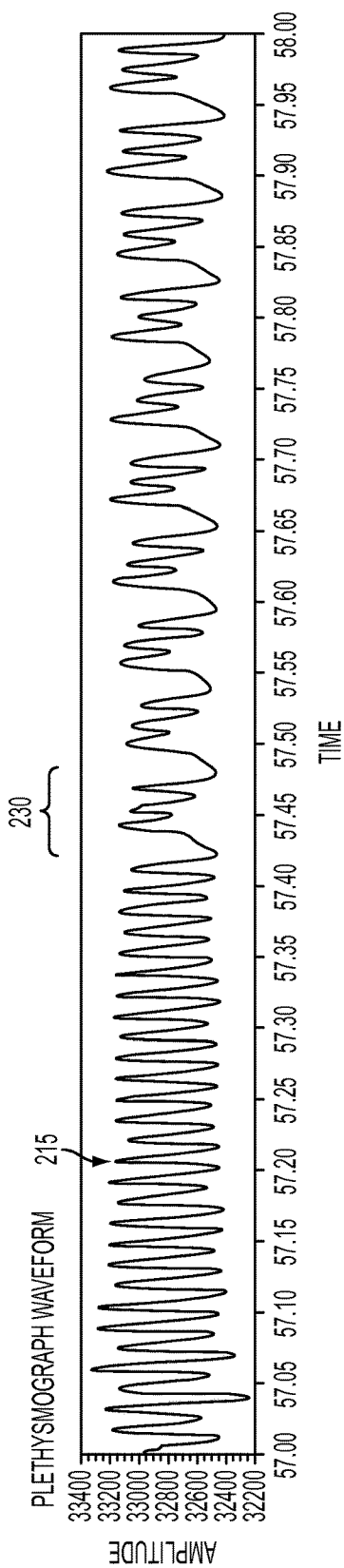
FIG. 2C depicts a human pulse volume waveform showing both normal peaks and peaks corresponding to premature ventricular contractions showing quadrigeminy in accordance with some embodiments.

FIG. 2C illustrates a group of normal pulse volume waveforms 215 followed by a group of abnormal pulse volume waveforms 230. The apparent triplet structure manifested in the abnormal pulse volume waveform 230 may demonstrate premature ventricular contractions indicating quadrigeminy. In contrast to the pulse volume waveform trace depicted in FIG. 2B, in which isolated abnormal pulse waveforms are observed, the pulse volume waveform trace depicted in FIG. 2C may indicate that the anomalous heart depolarizations are maintained over some period of time and may therefore represent a pathological condition.

Figure 2D:
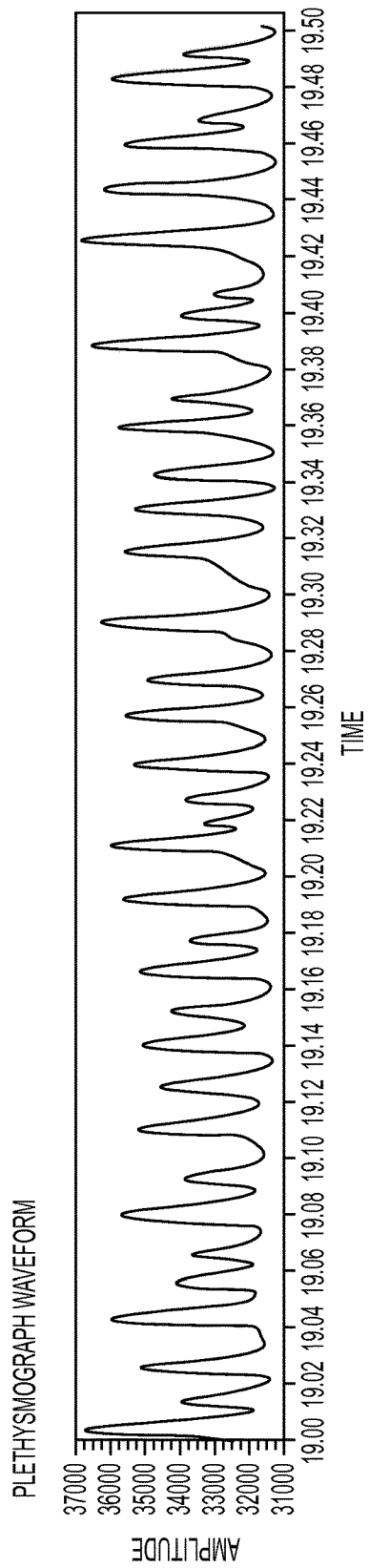
FIG. 2D depicts a human pulse volume waveform corresponding to a wide range of cardiac dysrhythmias in accordance with some embodiments.

FIG. 2D illustrates a group of abnormal pulse volume waveforms that do not appear to show any rhythmic or amplitude regularity. Such irregular pulse volume waveforms may be an indication for atrial fibrillation.

Figure 2E:
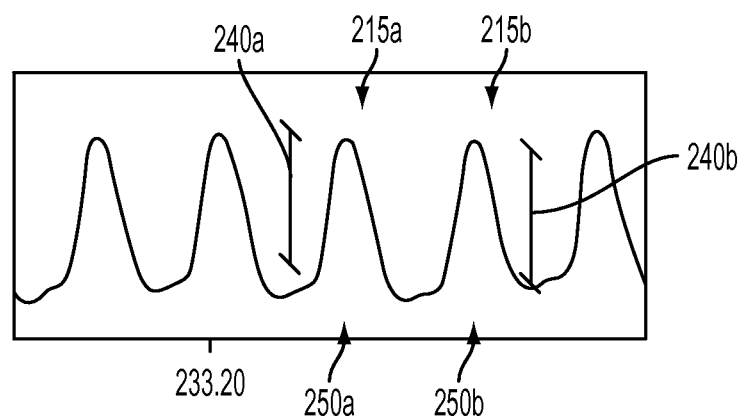
FIG. 2E depicts an expanded view of a portion of the porcine pulse volume waveform of FIG. 2B.

FIG. 2E depicts an expanded view of some pulse volume waveforms illustrated in FIG. 2B. While the ECG structure may be complex, as indicated by the PQRST waveforms as depicted in FIG. 1, pulse volume waveforms 215a,b may appear to have a simpler morphology. Such pulse volume waveforms 215a,b may generally be described as a plurality of single peaks, each of which is characterizable by a peak amplitude 240a,b (corresponding to peaks 215a and 215b, respectively) and a time of peak occurrence 250a,b (corresponding to peaks 215a and 215b, respectively). Additional characterizations may include a measure of peak width (such as half-width at half-maximum or full-width at half-maximum) and a measure of peak symmetry about the peak maximum. Other more complex characterizations of a single or multiple pulse volume waveforms may also be contemplated. As one non-limiting example, a pulse volume waveform peak amplitude difference may be calculated as the difference in peak amplitude between successive peaks 215a,b. As one example, a pulse volume waveform peak difference may be calculated as a difference between the peak amplitude 240b of pulse volume peak 215b and the peak amplitude 240a of pulse volume peak 215a. As another non-limiting example, a pulse volume waveform time occurrence difference may be calculated as the difference in peak time occurrence between successive peaks 215a,b. As an example, a pulse volume waveform time occurrence difference may be calculated as a difference between the peak occurrence time 250b of pulse volume peak 215b and the peak occurrence time 240a of pulse volume peak 215a.

Figure 3A:
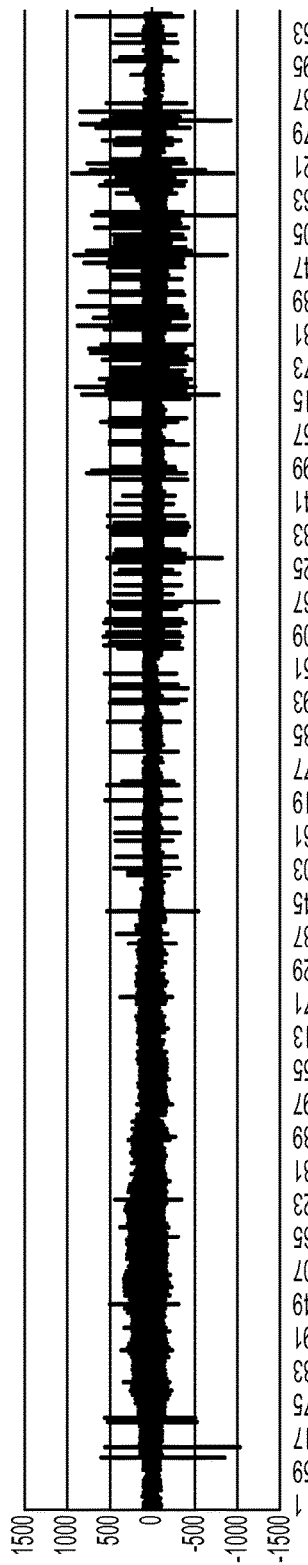
FIG. 3A depicts a display of pulse volume waveform peak amplitude differences in accordance with some embodiments.
Figure 3B:
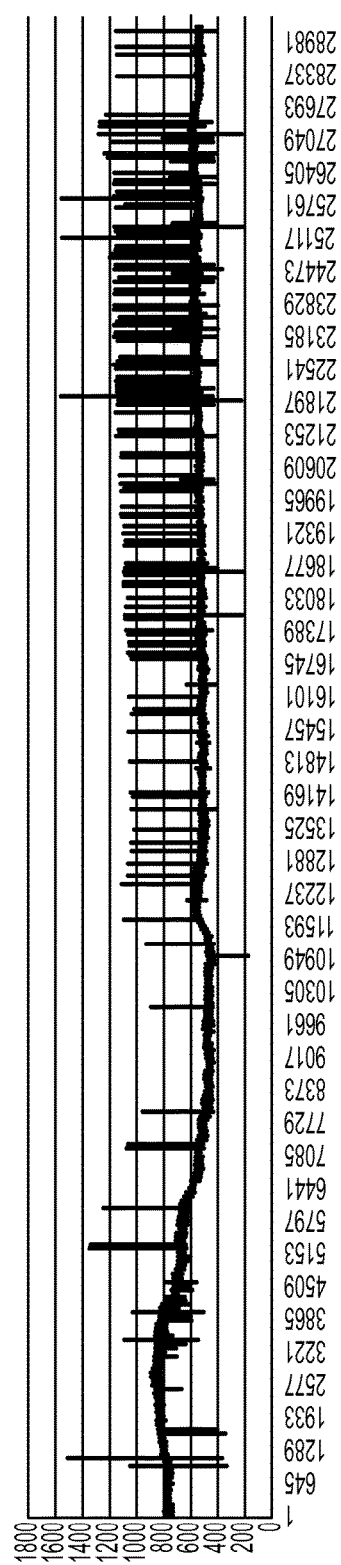
FIG. 3B depicts a display of pulse volume waveform peak time differences in accordance with some embodiments.

A time course display of successive peak amplitude differences and peak time occurrence differences may be used as an indication of patient cardiac status. FIGS. 3A and 3B depict non-limiting examples of such displays showing variations in peak amplitude differences (FIG. 3A) and peak time occurrence differences (FIG. 3B). It may be observed that significant changes in peak amplitude differences and peak time occurrence differences may occur at about the same time. However, significant changes in peak amplitude differences and peak time occurrence differences may also occur independently of each other.

Figure 4A:
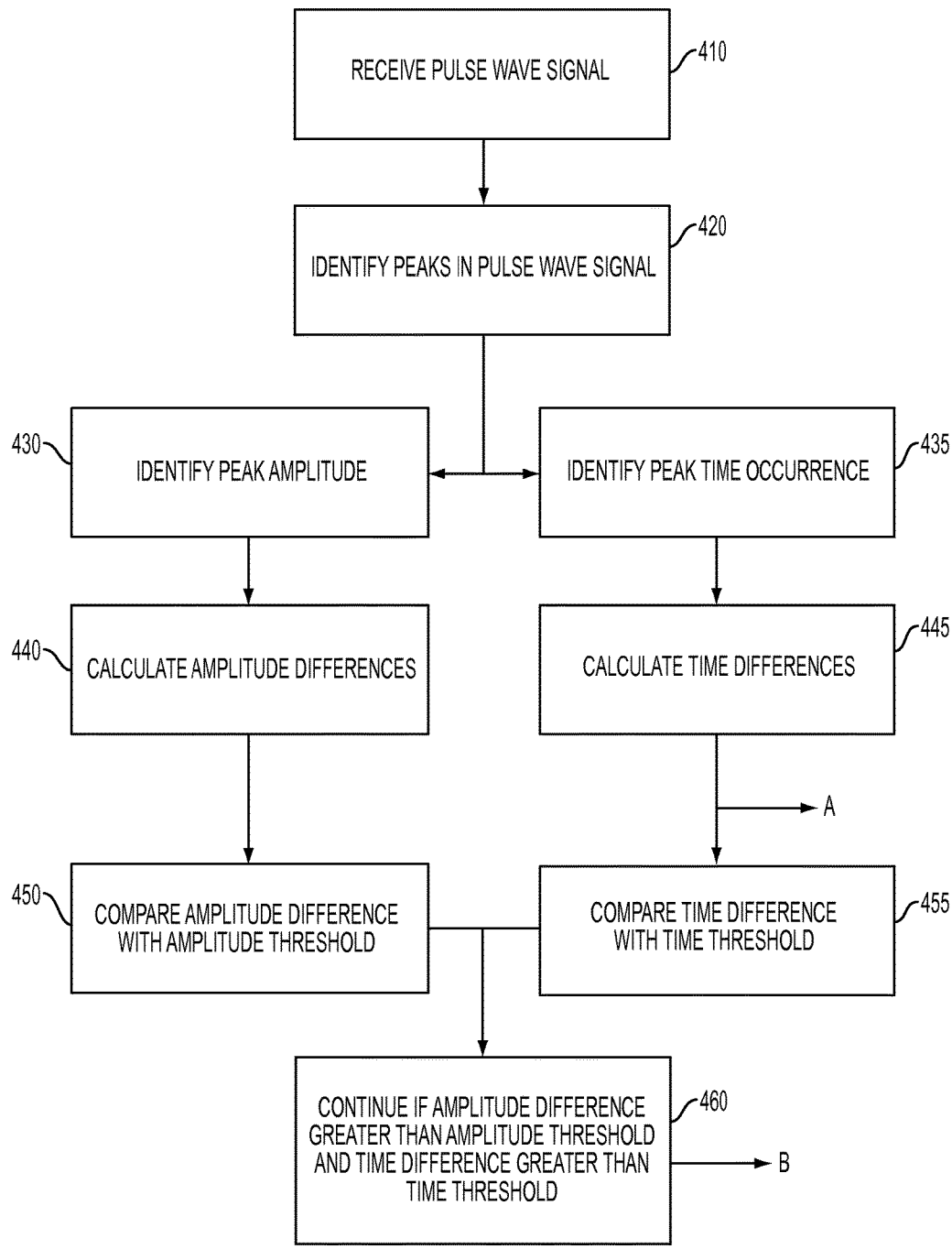
FIGS. 4A and 4B are flow charts for a method of identifying a cardiac dysrhythmia behavior in accordance with some embodiments.
Figure 4B:
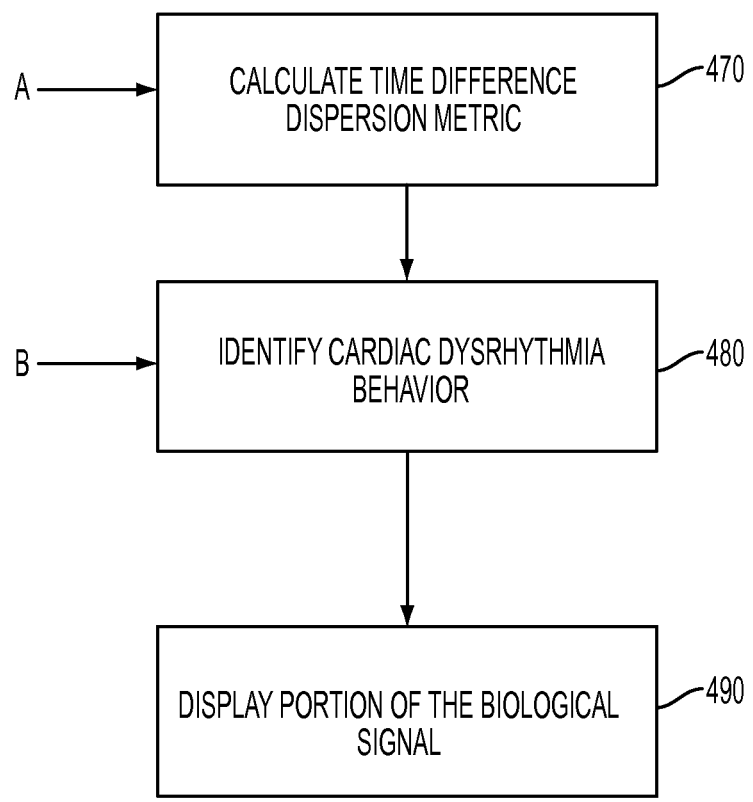

FIGS. 4A and 4B together constitute a flow chart of a method for identifying cardiac dysrhythmia behavior from a plurality of pulse volume waveforms.

A biological signal, emulating a plurality of arterial pulse volume waveforms, may be received 410 by a computing device from a sensor associated with a human body such as from a patient undergoing a therapeutic procedure. Non-limiting embodiments of such a sensor may include one or more of a plethysmograph, a transmittance photo-optic sensor, a reflective photo-optic sensor, a pressure transducer, a tonometry device, a strain gauge, an ultrasound device, an electrical impedance measurement device, and a radar device. In one non-limiting example, the sensor may be a photoplethysmograph. Such sensors may be in physical contact with the patient's skin surface, within the patient, or may be placed at some distance from the patient.

The computing device may identify 420 the occurrence of pulse volume peaks within the plurality of pulse volume waveforms. In some non-limiting embodiments, the computing device may identify 420 the pulse volume peaks based on maximum pulse volume peak amplitudes, minimum pulse volume amplitudes, or fitting at least a portion of one or more of the pulse volume waveforms to a mathematical model, such as a parabola.

The computing device may identify 430 or calculate a peak amplitude value for each of the pulse volume peaks. The computing device may further calculate 440 a difference between peak amplitudes. In some embodiments, the difference between peak amplitudes may be calculated for any two peaks, regardless of the times of their occurrences. In some non-limiting embodiments, the amplitude difference calculated 440 by the computing device may correspond to an amplitude difference between succeeding peaks (that is, a difference in amplitude between a first peak and a second peak occurring immediately thereafter).

The computing device may also identify 435 the time at which each pulse volume peak occurs. The computing device may further calculate 445 a difference between peak time occurrences. In some embodiments, the difference between peak time occurrences may be calculated for any two peaks, regardless of the times of their occurrences. In some non-limiting embodiments, the time occurrence difference (or time difference) calculated 445 by the computing device may correspond to a time difference between succeeding peaks (that is, a time difference between a first peak and a second peak occurring immediately thereafter).

The computing device may compare 450 each amplitude difference with an amplitude difference threshold. In one embodiment, the amplitude difference threshold may be provided to the computing device by a computing device user. In another embodiment, the amplitude difference threshold may be calculated by the computing device. In some non-limiting examples, the computing device may calculate the amplitude difference threshold from an amplitude difference baseline plus an amplitude difference offset. In one non-limiting example, the amplitude difference baseline may be calculated by the computing device from at least a portion of peak amplitude differences occurring within a data window. The data window may be characterized by one or more of a start time, a stop time, and a window duration. In some non-limiting examples, the data window may have a window duration of about 1 minute to about 24 hours. Non-limiting examples of such time window durations may include time durations of about 1 minute, about 2 minutes, about 5 minutes, about 10 minutes, about 20 minutes, about 30 minutes, about 1 hour, about 2 hours, about 5 hours, about 10 hours, about 20 hours, about 24 hours, and ranges between any two of these values including endpoints. Values characterizing the data window may include static values accessible by the computing device, one or more values supplied by a computing device user, or a combination thereof.

In some non-limiting examples, the amplitude difference baseline may be calculated as an average of peak amplitude differences of at least a portion of peak amplitude differences occurring within the data window. In other non-limiting examples, the amplitude difference baseline may be calculated as the maximum peak amplitude difference of at least a portion of peak amplitude differences occurring within the data window. In some non-limiting examples, the data window may be chosen to include one or more pulse volume waveforms for a patient showing normative cardiac activity as determined either by the pulse volume waveforms or an ECG waveform. In some non-limiting examples, the amplitude difference offset may be calculated from the average of peak amplitude differences.

Non-limiting examples of such amplitude difference offsets may be calculated as fractions of the amplitude difference baseline, for example the value of the average peak amplitude difference. Examples of such fractions may include 0.05, 0.1, 0.15, 0.2, 0.25, 0.3, 0.35, 0.4, 0.45, 0.5, and ranges between any two of these values including endpoints. In some non-limiting embodiments, the fraction used to calculate the amplitude difference offset may be derived from the variability of normative peak amplitude differences from the patient. In another non-limiting embodiment, the fraction used to calculate the amplitude difference offset may be derived from the variability of normative peak amplitude differences of a group of patients. Thus, a non-limiting range in values of the amplitude threshold may include values of about 1.05 to about 1.5 times the amplitude difference baseline. In some embodiments, the non-limiting range in values of the amplitude threshold may include values of about 1.05 to about 1.5 times the average of amplitude differences. In other embodiments, a non-limiting value of the amplitude threshold may be about 1.2 times the peak amplitude baseline.

The computing device may compare 455 each time difference with a time difference threshold (or time threshold). In one embodiment, the time threshold may be provided to the computing device by a computing device user. In another embodiment, the time threshold may be calculated by the computing device. In some non-limiting examples, the computing device may calculate the time threshold from a peak time difference baseline plus a peak time difference offset. In one non-limiting example, the peak time difference baseline may be calculated by the computing device from at least a portion of peak time differences occurring within a data window. The data window may be characterized by one or more of a start time, a stop time, or a window duration. In some non-limiting examples, the data window may have a window duration of about 1 minute to about 24 hours. Non-limiting examples of such time window durations may include time durations of about 1 minute, about 2 minutes, about 5 minutes, about 10 minutes, about 20 minutes, about 30 minutes, about 1 hour, about 2 hours, about 5 hours, about 10 hours, about 20 hours, about 24 hours, and ranges between any two of these values including endpoints. Values characterizing the data window may include static values accessible by the computing device, one or more values supplied by a computing device user, or a combination thereof.

In some non-limiting examples, the peak time difference baseline may be calculated as the reciprocal of the patient's average normative pulse rate. In one non-limiting example, if a patient's average pulse rate is 1 bpm (1 beat per minute), the peak time difference baseline may be 1000 msec. In other non-limiting examples, the peak time difference baseline may be calculated from a histogram of a plurality of peak time differences (see below). In one non-limiting example, the peak time difference baseline may be calculated as the peak time difference having the greatest number of occurrences in the histogram. In some non-limiting examples, the plurality of peak time differences in the histogram may be chosen during a time window in which the patient demonstrates normative cardiac activity as determined either by the pulse volume waveforms or an ECG waveform.

Non-limiting examples of such peak time difference offsets may be calculated as fractions of the peak time difference baseline, for example the value of the peak time difference having the greatest number of occurrences in the histogram. Examples of such fractions may include 0.05, 0.1, 0.15, 0.2, 0.25, 0.3, 0.35, 0.4, 0.45, 0.5, and ranges between any two of these values including endpoints. In some non-limiting embodiments, the fraction used to calculate the peak time difference offset may be derived from the width of a peak in the time difference histogram corresponding to the patient normative pulse rate. In another non-limiting embodiment, the fraction used to calculate the peak time difference offset may be derived from the variability of normative pulse rates taken from a group of patients. Thus, a non-limiting range in values of the time threshold may include values of about 1.05 to about 1.5 times the peak time difference baseline. In other embodiments, a non-limiting value of the time threshold may be about 1.2 times the peak time difference baseline.

In addition to comparing each of the plurality of time differences with a time threshold, the computing device may also calculate 470 one or more time difference dispersion metrics from at least some portion of time differences. In one non-limiting embodiment, calculating 470 one or more time difference dispersion metrics may include calculating a histogram from at least a portion of the plurality of time differences and calculating, by the computing device, the at least one time difference dispersion metric from the histogram. In one non-limiting example, the histogram may be calculated from peak time differences occurring within a data window. The data window may be characterized by one or more of a start time, a stop time, or a window duration. In some non-limiting examples, the data window may have a window duration of about 1 minute to about 24 hours. Non-limiting examples of such time window durations may include time durations of about 1 minute, about 2 minutes, about 5 minutes, about 10 minutes, about 20 minutes, about 30 minutes, about 1 hour, about 2 hours, about 5 hours, about 10 hours, about 20 hours, about 24 hours, and ranges between any two of these values including endpoints. One skilled in the art may recognize that a number of metrics may be determined to characterize features found within a histogram. Some non-limiting examples may include one or more of a maximum value of at least one histogram peak, a value of a width metric of the at least one histogram peak, and a histogram difference time corresponding to the maximum value of the at least one histogram peak. Any one or more of such histogram metrics may be used to calculate the one or more time difference dispersion metrics. Examples of such histograms and metrics derived therefrom are discussed in more detail with respect to FIGS. 6A-6D, disclosed below.

It may be understood that each pair of pulse volume waveform peaks has an associated amplitude difference and an associated time difference. Criteria 460 for identifying a cardiac dysrhythmia behavior may include a requirement that the amplitude difference between a pair of pulse volume waveform peaks exceeds the amplitude threshold, and the time difference associated with the same pair of pulse volume waveform peaks exceeds the time threshold. It may be understood that an amplitude difference exceeding the amplitude threshold may be considered an anomalous amplitude difference. It may be further understood that a time difference exceeding the time threshold may be considered an anomalous time difference. Consequently, the pair of pulse volume waveform peaks giving rise to the anomalous amplitude difference and anomalous time difference may also be considered anomalous.

Dysrhythmic behavior may be identified 480 based on the above criteria 460 along with the one or more time difference dispersion metrics. As one non-limiting example, in addition to the above disclosed criteria 460, a pulse time difference that exceeds a histogram difference time corresponding to the time difference associated with a patient normative pulse rate may be used to identify 480 a dysrhythmia event. In another non-limiting example, in addition to the above disclosed criteria 460, the appearance of multiple histogram peaks may be used to identify 480 a dysrhythmia event. In another non-limiting example, in addition to the above disclosed criteria 460, a histogram peak associated with a patient normative pulse rate having a histogram peak width that exceeds the normative peak width associated with the patient normative pulse rate may be used to identify 480 a dysrhythmia event.

Additionally, the one or more time difference dispersion metrics may be used for other purposes. In one example, an algorithm to calculate an amplitude threshold value or a time threshold value may be chosen, by the computing device, based on the one or more time difference dispersion metrics. Thus, as one example, the amplitude threshold value may be calculated from an average of pulse amplitudes for one value of at least one dispersion metric. Alternatively, the amplitude threshold value may be calculated from a maximum value of pulse amplitudes for a different value of at least one dispersion metric.

The biological signal, along with any one or more of the amplitude difference, time difference, time difference histograms, or time difference dispersion metrics may be displayed 490 by the computing device.

Figure 5:
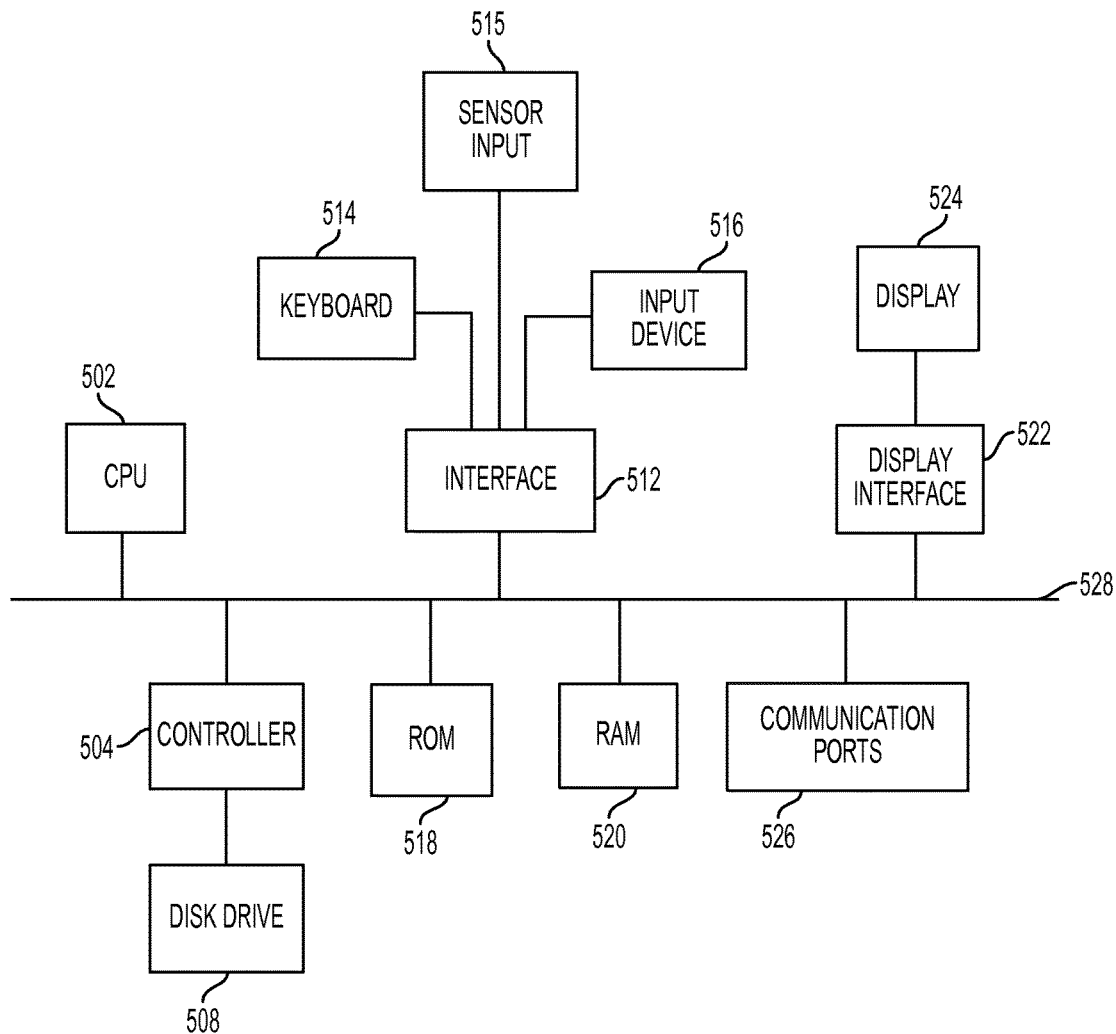
FIG. 5 depicts a schematic of a computing device in accordance with some embodiments.

FIG. 5 is a block diagram of an embodiment of at least some components that may compose the computing device. Referring to FIG. 5, a bus 528 may serve as the main information highway interconnecting the other illustrated components of the hardware. CPU 502 is the central processing unit of the system, performing calculations and logic operations required to execute at least some calculations for the method. Read only memory (ROM) 518 is one non-limiting example of a static or non-transitory memory device, and random access memory (RAM) 520 is one non-limiting example of a transitory or dynamic memory device.

A controller 504 may interface the system bus 528 with one or more optional disk drives 508. These disk drives may include, for example, external or internal DVD drives, CD ROM drives, or hard drives.

Program instructions for calculations or other computing device functions may be stored in the ROM 518 and/or the RAM 520. Optionally, program instructions may be stored on one or more computer readable media such as a compact disk, a digital disk, and other recordable media. Alternatively, program instructions may be provided to the computing device via a communications signal or a carrier wave. Additionally, pulse volume waveform data or other data used by the computing device may be stored on one or more removable memory devices that may include, as non-limiting examples, a removable disc, a removable card, a removable memory stick, a flash drive, a removable SIM chip, a writable CD-ROM or DVD disk, and/or a miniature data tape. Such devices may be used to transfer data from the computing device to another data receiving device such as a home computer.

An optional display interface 522 may permit information from the bus 528 to be displayed on a display device 524 in audio, graphic, or alphanumeric format. Additional output interface devices may include a printer, a barcode printer, an LCD panel device, a touch screen device, an audio device, an LED panel, an OLED panel device, one or more individual LEDs, either as separate displays or grouped together, and a haptic device. Communication with external devices may occur using various communication ports 526.

In addition to the components disclosed above, the computing device may also include an interface 512 which may allow for receipt of data from input devices such as a keyboard 514 or other input devices 516 such as a touch screen, a mouse, a remote control, a pointing device, a pushbutton, a haptic device, a voice recognition device, a proximity sensor, a motion detection sensor, a directional pad, and/or a joystick.

In addition, biological signals acquired by a pulse volume sensor may be communicated to the computing device via a sensor input 515 through the interface 512 to the bus 528. Such biological signals may be presented to the computing device as either analog signals or digital signals. If the pulse volume sensor provides analog biological signals, the computing device may also include hardware components configured to convert the analog signals into digital signals. Non-limiting examples of such hardware components may include one or more of a sample and hold device, an analog-to-digital converter, and a voltage reference. Such hardware components may be present as independent devices, one or more combination devices, or one or more detachable modules that may be placed in data communication with the sensor input 515, the interface 512, or the bus 528. If the pulse volume sensor provides digital biological signals, the computing device may include one or more separate digital interfaces to receive the digital biological signals. Such digital interfaces may include, without limitation, one or more of a parallel interface, a serial interface, an IR interface, a radio frequency interface, and a personal area network interface.

It may be appreciated that such a computing device may receive sensor data from additional biological signal detectors including, without limitation, an ECG device, a patient temperature measurement device, a patient respiratory measurement device, and a patient heart rate measurement device. In some embodiments, biological signal data from these or other biological signal detecting devices may be used as part of the method for identifying or characterizing cardiac dysrhythmia behavior.

The computing device may also be configured to receive data from additional devices such as from one or more therapeutic devices including, for example, a dialysis device or a ventilator. Data from such therapeutic devices may be included in one or more output displays by the computing device to assist a health care professional in correlating a cardiac dysrhythmia behavior with the operation of the one or more therapeutic devices. In some non-limiting examples, the computing device may include instructions to predict possible cardiac dysrhythmia behavior based on data from the one or more therapeutic devices along with biological signal data from the one or more biological signal detecting devices.

A time difference dispersion may be defined as the amount of variation in the time difference between the time occurrences of successive pulse waveform peaks. Time difference dispersion may be represented graphically in any number of formats as known to those with skill in the art. One example of a graphical display of dispersion may include a histogram. A histogram is a graph of the number of occurrences of each of a number of data values taken within a sample window. FIGS. 6A-D depict examples of histograms displaying the dispersion of the time difference between successive pulse waveform peaks.

Figure 6A:
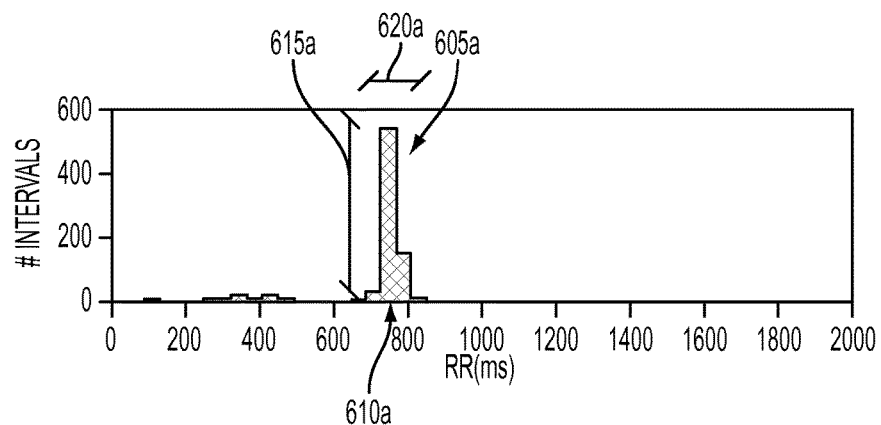
FIG. 6A depicts a normal human time difference dispersion histogram in accordance with some embodiments.

FIG. 6A illustrates a histogram of time differences between successive pulse waveform peaks for a patient showing normative (typical or non-pathological) electrocardiac behavior. The histogram in FIG. 6A is composed of a narrow primary peak 605*a* centered around a primary time difference 610*a* of about 750 msec. The primary peak 605*a* may represent a normal pulse time (reciprocal pulse rate) corresponding to a pulse rate of about 45 bpm (beats per minute). The primary peak 605*a* may be characterized by any number of dispersion metrics including, for example, a primary time difference 610*a* and a primary amplitude 615*a*. The primary peak 605*a* may also be characterized by a primary peak width 620*a*. A histogram peak width metric may be calculated according to any method known to one skilled in the art including, without limitation, a half-width at half-maximum (HWHM) or a full-width at half-maximum (FWHM). More complex metrics for the width of the hisogram peak may be derived from a fit of the peak to a known curve (such as a Gaussian function) having known parameters associated with the curve spread (such as a Guassian function σ parameter).

Figure 6B:
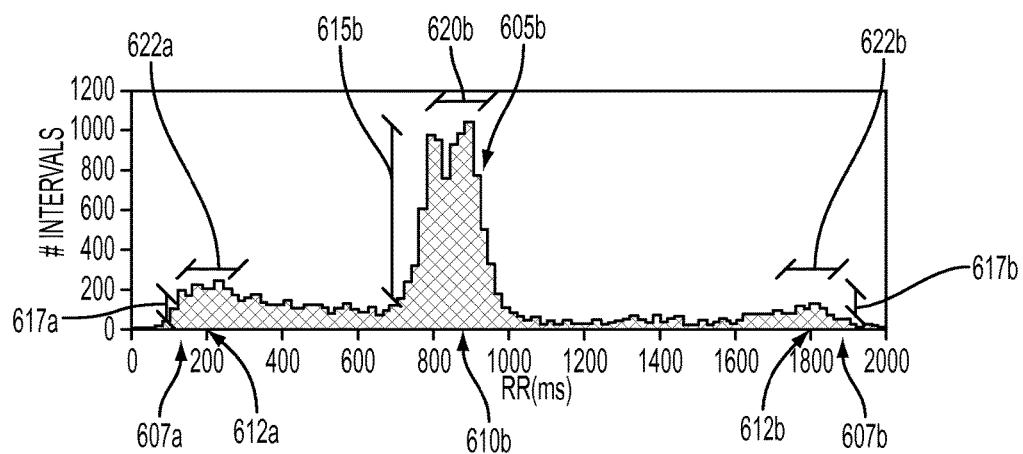
FIG. 6B depicts a human time difference dispersion histogram illustrating quadrigeminy premature ventricular contractions in accordance with some embodiments.

FIG. 6B illustrates a histogram of time differences between successive pulse waveform peaks for a patient having multifocal premature ventricular beats. The histogram in FIG. 6B is composed of a symmetric primary peak 605*b* centered around a primary time difference 610*b* of about 900 msec along with two secondary peaks 607*a,b* centered around respective secondary time differences 612*a,b* of about 200 msec and about 1800 msec. The primary peak 605*b* may be characterized by any number of dispersion metrics including, for example, a primary time difference 610*b* and a primary amplitude 615*b*. The primary peak 605*b* may also be characterized by a primary peak width 620*b*. In FIG. 6B, it may be observed that the two secondary peaks 607*a,b* do not appear to be symmetric based on their respective secondary peak widths 622*a,b*. The two secondary peaks 607*a,b* may be characterized by any number of dispersion metrics including, for example, secondary time differences 612*a,b* (respectively) and secondary amplitudes 617*a,b* (respectively). Although a histogram peak width metric associated with the primary peak width 620*b* may be readily described by a single value, such as HWHM or FWHM, a more complex description of a histogram peak width metric for the two secondary peaks 615*b,c* may be required based on the asymmetry of their respective widths 622*a,b*.

Figure 6C:
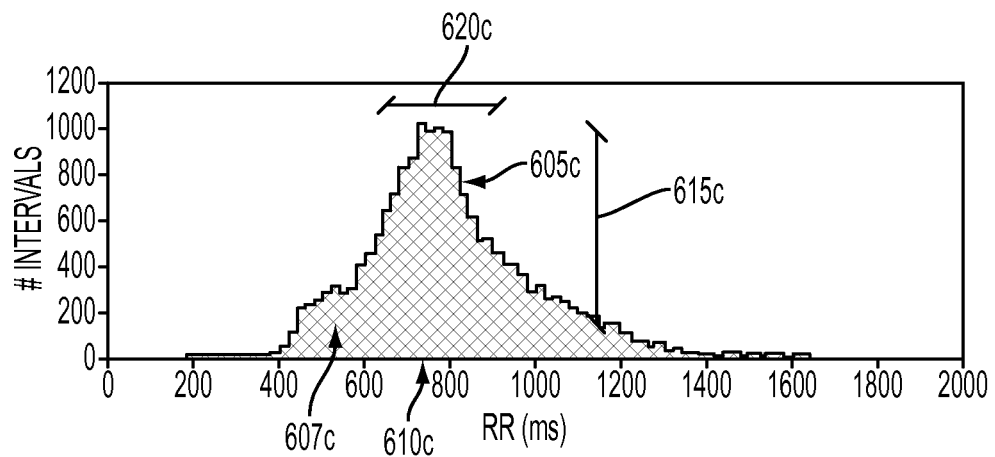
FIG. 6C depicts a time difference dispersion histogram illustrating a large variation in peak time differences in accordance with some embodiments.

FIG. 6C illustrates a histogram of time differences between successive pulse waveform peaks for a patient with atrial fibrillation showing general variability of the R-R time interval in the ECG. The histogram in FIG. 6C is composed of a broad asymmetric primary peak 605*c* having a peak amplitude 615*c* located at a primary time difference 610*c* of about 800 msec. The broad asymmetric primary peak 605*c* may be the only detectable peak in the histogram. Alternatively, the primary peak 605*c* may overlap to some extent a secondary peak 607*c*. The primary peak 605*c* may be characterized by any number of dispersion metrics including, for example, a primary time difference 610*c* and a primary amplitude 615*c*. The primary peak 605*c* may also be characterized by a primary peak width 620*c*. More complex analyses of FIG. 6C may further include a decomposition of the histogram into two overlapping peaks, each separately characterized by one or more histogram metrics.

Figure 6D:
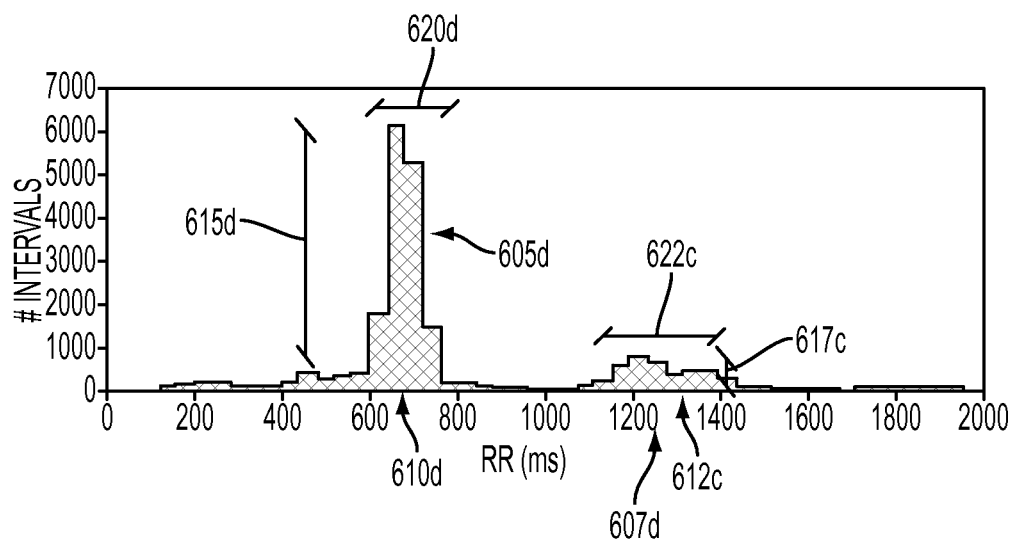
FIG. 6D depicts a time difference dispersion histogram illustrating supraventricular tachycardia in accordance with some embodiments.

FIG. 6D illustrates a histogram of time differences between successive pulse waveform peaks for a patient showing supraventricular tachycardia. The histogram in FIG. 6D is composed of a narrow symmetric primary peak 605*d* having a peak amplitude 615*d* located at a primary time difference 610*d* of about 700 msec. The primary peak 605*d* may be characterized by any number of dispersion metrics including, for example, a primary time difference 610*d* and a primary amplitude 615*d*. The primary peak 605*d* may also be characterized by a primary peak width 620*d*. At least one secondary peak 607*d* centered around a secondary time difference 612*c* of about 1300 msec may also be observed. Alternatively, the observed secondary peak 607d may be composed of two closely spaced peaks including some overlap. The observed secondary peak 607d may be characterized by a secondary peak amplitude 617c and secondary peak width 622c. More complex analyses of FIG. 6D may further include a decomposition of the observed secondary peak 607e into two overlapping peaks, each separately characterized by one or more histogram metrics.

It may be understood that the histogram metrics disclosed above with respect to FIGS. 6A-6D constitute non-limiting examples, and other metrics derived from analyses of such histograms are also anticipated. Any one or more of the time difference histogram metrics may be incorporated into the method as one or more time difference dispersion metrics. Alternatively, the one or more time difference histogram metrics may be used by the computing device to calculate additional time difference dispersion metrics.

It may further be recognized that the sample histograms presented in FIGS. 6A-6D may be taken merely as representative histograms for each of the identified arrhythmic behaviors, and should not be identified as being definitively diagnostic of the identified arrhythmic behaviors. Alternative histograms may be obtained from patients diagnosed with any of the identified arrhythmic behaviors, and patients having arrhythmic behaviors not otherwise specified hereinabove may provide histograms similar to those depicted in FIGS. 6A-6D.

EXAMPLES

Example 1: An Annotated Output Display of Pulse Waveform Data

Figure 7:
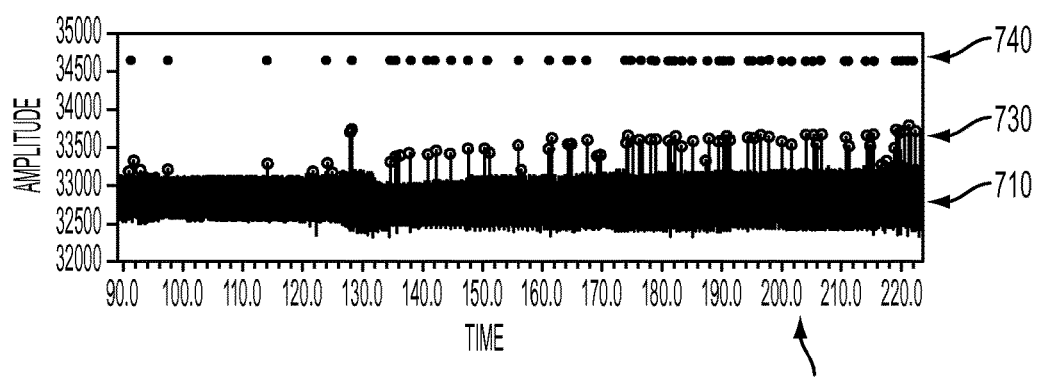
FIG. 7 depicts an annotated output display of pulse volume waveform data showing increasing numbers of premature ventricular contractions in accordance with some embodiments.

FIG. 7 illustrates an example of at least a portion of an annotated output display of porcine pulse waveform data. In one non-limiting embodiment, the display may be presented to a user as an updated series of static snapshots taken during successive time windows of pulse waveform data. In another non-limiting embodiment, the display may be a continuously scrolling display over time. In some embodiments, the display may include a display of data 710 calculated from the pulse waveforms obtained by the sensor. Such displayed data 710 may include one or more of raw sensor data, filtered sensor data, and amplified sensor data. The output display may also include a time scale 720 to indicate times associated with features in the displayed data 710. In some non-limiting examples, the display may be annotated with any number of indicia to provide visual information to the user regarding the displayed data 710. Indicia may include peak indicia 730 to note the occurrence of pulse waveform peaks. Indicia may also include dysrhythmia indicia 740 to alert a user that of one or more coronary dysrhythmia events. In some non-limiting embodiments, dysrhythmia indicia 740 may also include visual cues (such as color coding or shape coding) to inform the user of the type of dysrhythmia event.

Figure 8A:
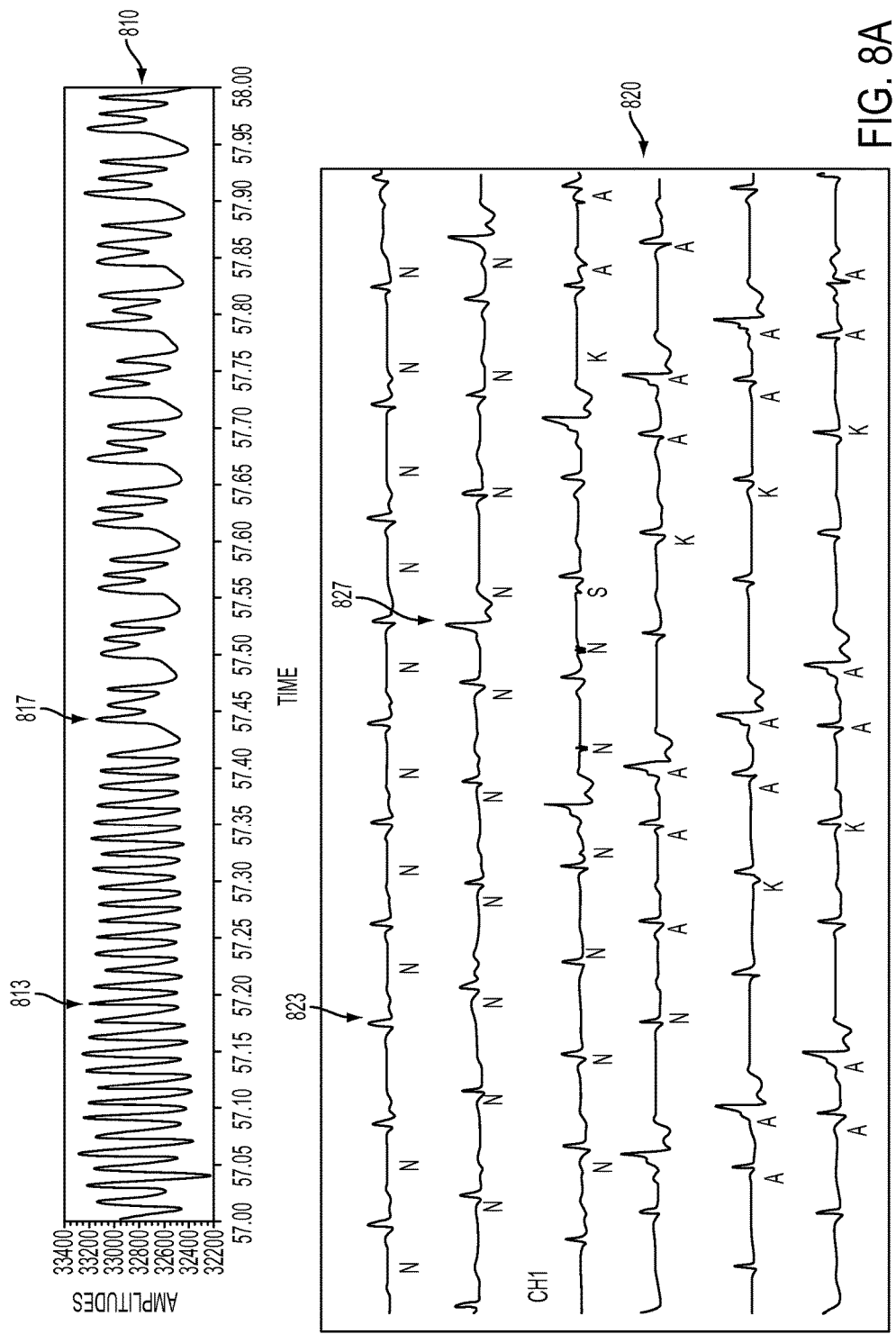
FIG. 8A depicts human pulse volume waveforms and ECG traces associated with quadrigeminy premature ventricular contraction patterns in addition to the pulse volume and ECG dispersion histograms in accordance with some embodiments.
Figure 8A:
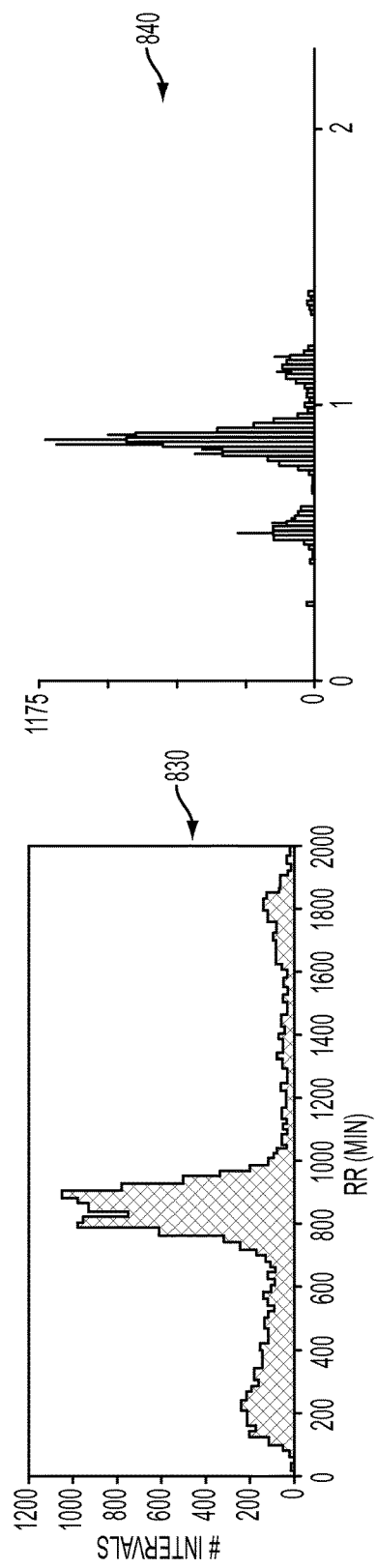

Example 2: Pulse Volume Waveform and ECG Trace Data with Related Dispersion Histograms FIG. 8A illustrates an example of the relation of a pulse volume waveform trace 810 to its associated ECG trace 820, specifically for a patient demonstrating quadrigeminy premature ventricular contractions. The pulse volume waveform trace 810 begins with normal pulse volume waveforms 813 that transition to quadrigeminy premature ventricular contractions 817 that are maintained for the duration of the trace. The ECG trace 820, taken concurrently with the pulse volume waveform trace 810, shows similar behavior. It may be observed that the ECG trace 820 begins with ECG waveforms showing normal morphology 823 that then transition to ECG waveforms showing anomalous morphologies 827. Although the time scale displays of the pulse volume waveform trace 810 and its associated ECG trace 820 are not identical, the change in the pulse volume waveform morphology occurs at the same time as the change in ECG waveform morphology. In this manner, it can be observed that the pulse volume waveforms may be used to indicate changes in cardiac contractility.

Dispersion analyses of the pulse volume waveform trace 810 and ECG waveform trace 820 are also depicted in FIG. 8A. A histogram of time differences between successive pulse volume waveforms 830 depicts a broad, symmetric central peak surrounded by two smaller and asymmetric peaks (see also FIG. 6B). A histogram of R-R interval times (from the ECG) 840 depicts a similar morphology as the time difference histogram of successive pulse volume waveforms 830.

Figure 8B:
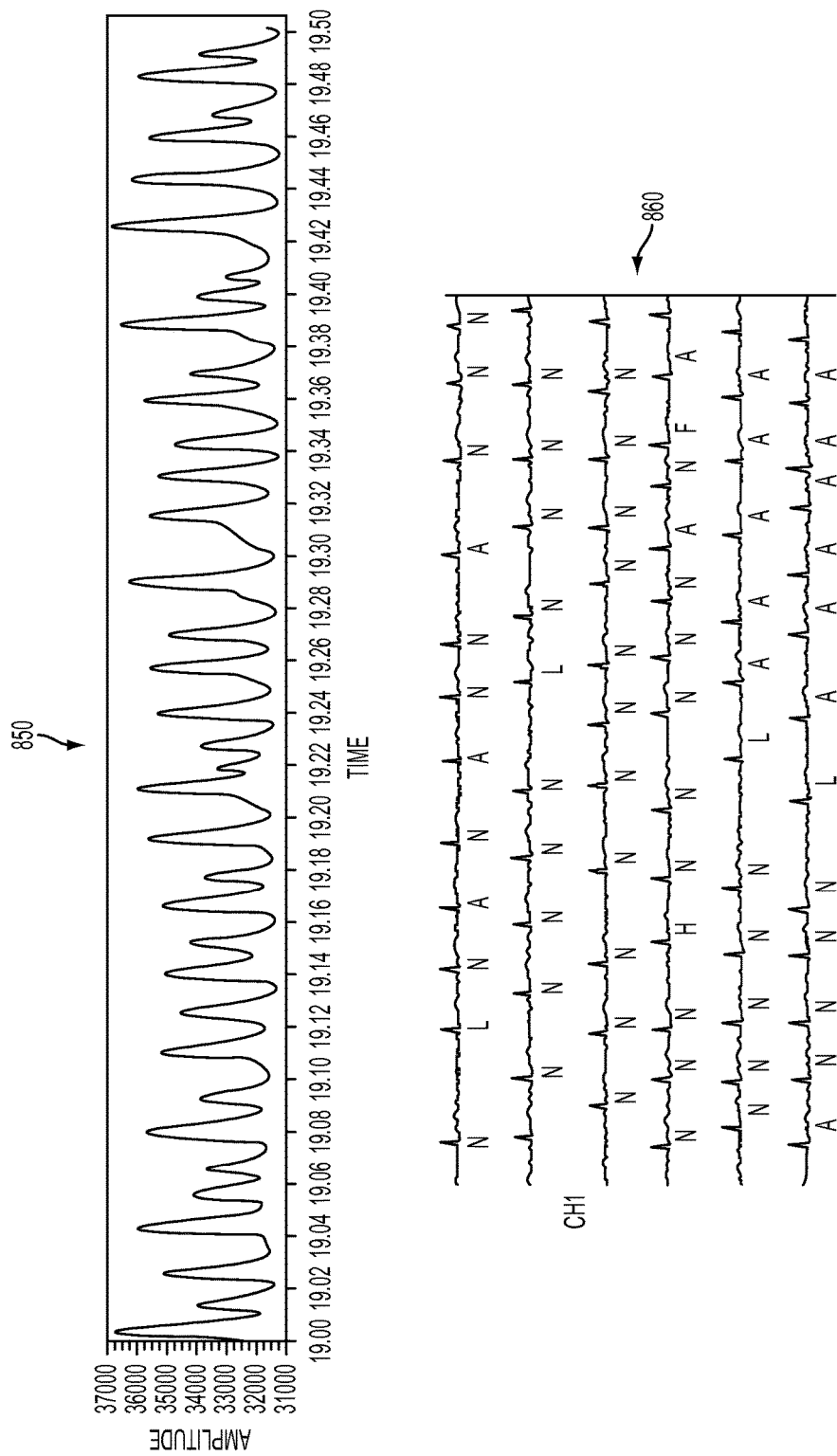
FIG. 8B depicts human pulse volume waveforms and ECG traces associated with a large variation in peak time differences in a patient with atrial fibrillation in addition to the pulse volume and ECG dispersion histograms in accordance with some embodiments.
Figure 8B:
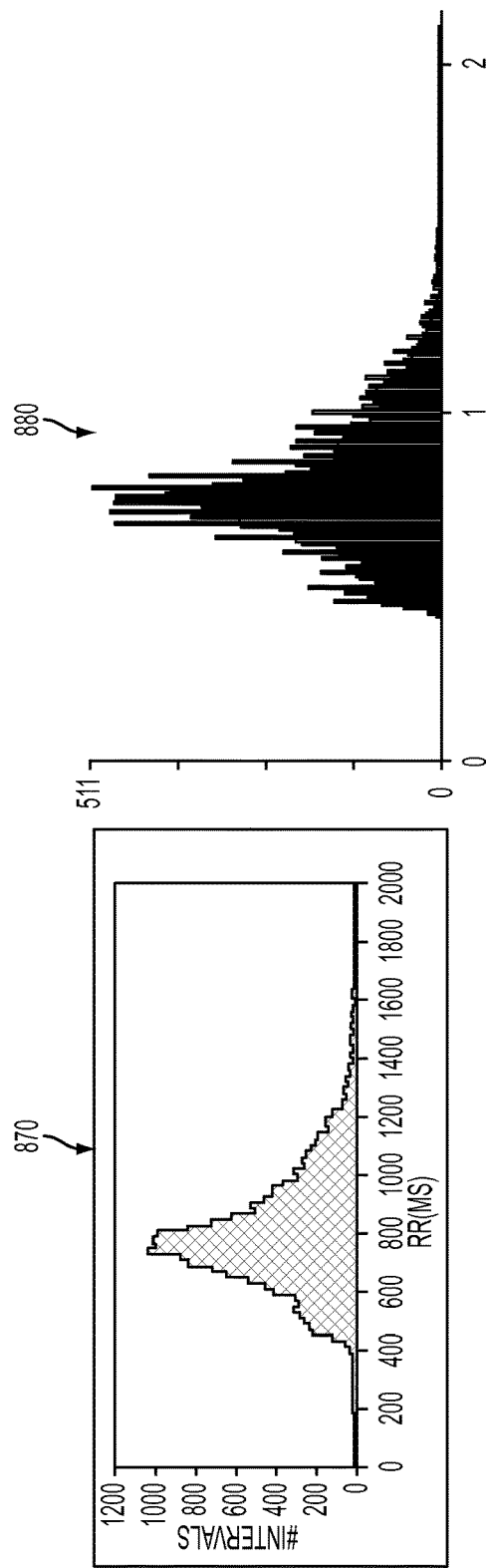

FIG. 8B illustrates an example of the relation of a pulse volume waveform trace 850 to its associated ECG trace 860, specifically for a patient demonstrating a wide variation in cardiac contractility. Both the pulse volume waveform trace 850 and the concurrently obtained ECG trace 860 depict similar irregular behavior. Dispersion analyses of the pulse volume waveform trace 850 (see also FIG. 6C) and ECG waveform trace 860 were calculated as disclosed above. A histogram of time differences between successive pulse volume waveforms 870 and a histogram of R-R interval times (from the ECG) 880 were obtained by this method. While the time course variation in the pulse volume waveforms and the ECG waveforms may be difficult to interpret, it is clear that the relevant dispersion histograms 870 and 880 show nearly identical morphologies. It may be appreciated, therefore, that detailed metrics regarding cardiac contractility may be obtained by appropriate analyses of the simpler waveforms presented by pulse volume data.

Figure 9:
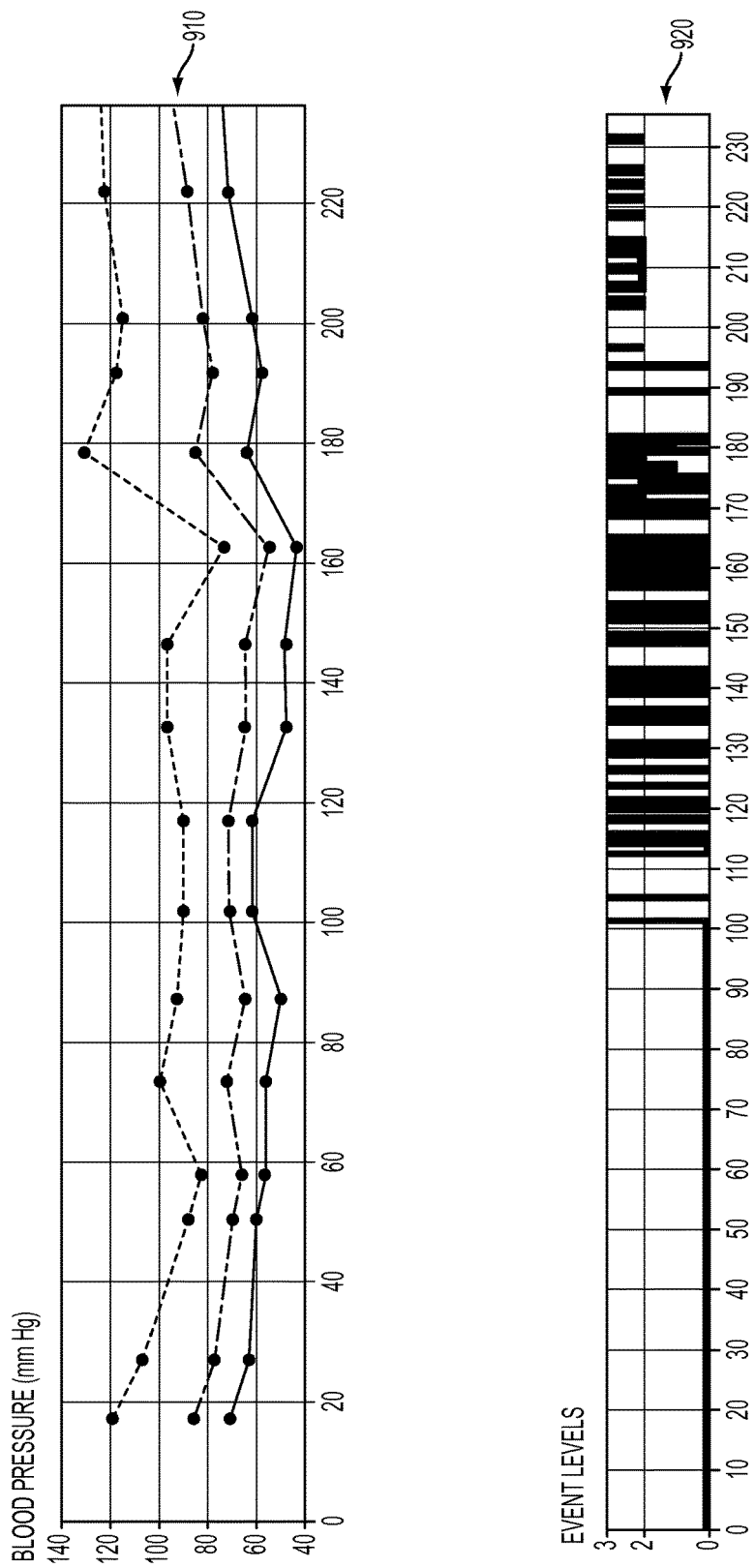
FIG. 9 depicts an annotated output display of patient data for a patient undergoing dialysis therapy in accordance with some embodiments.
Figure 9:
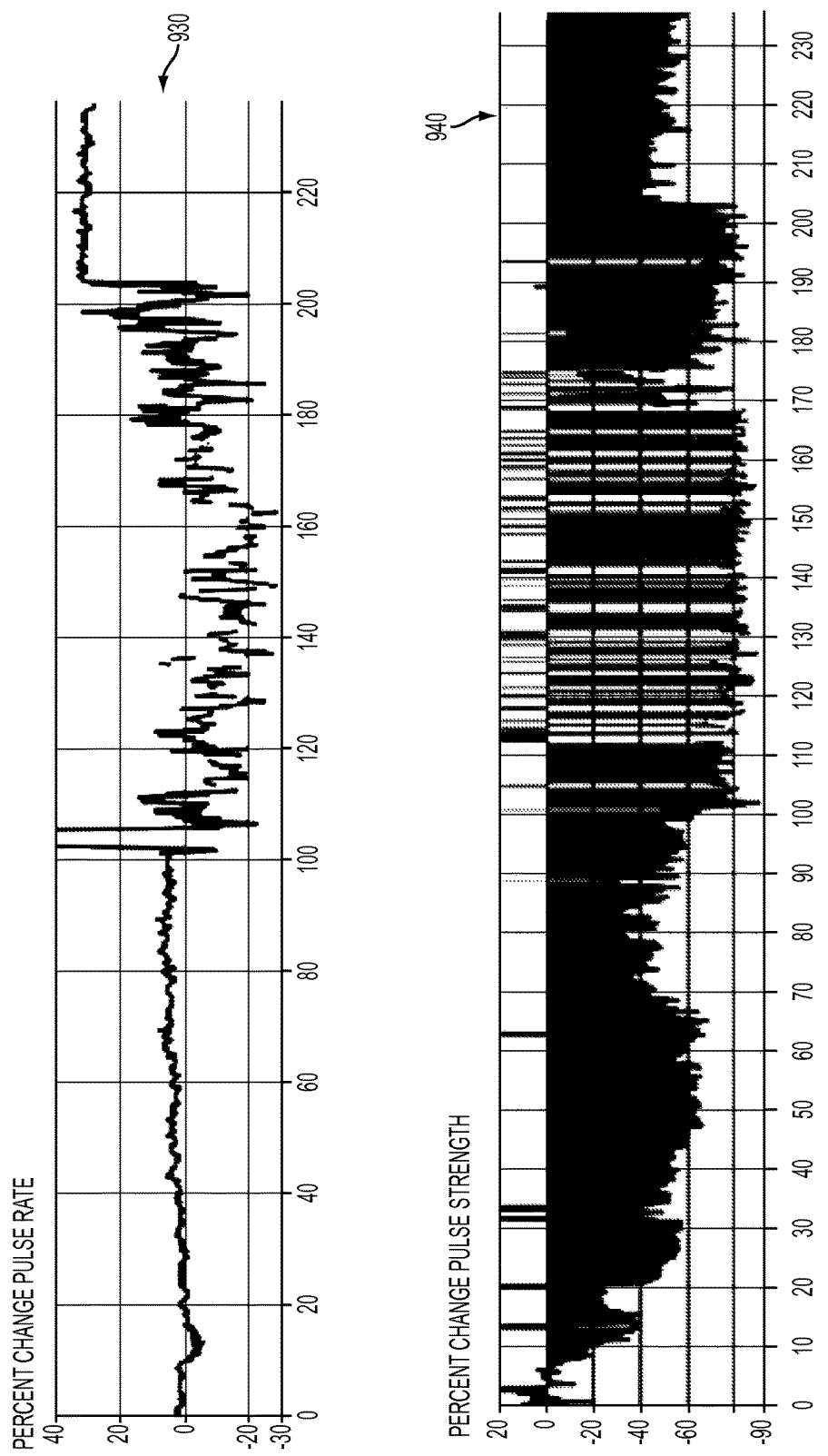
Figure 9:
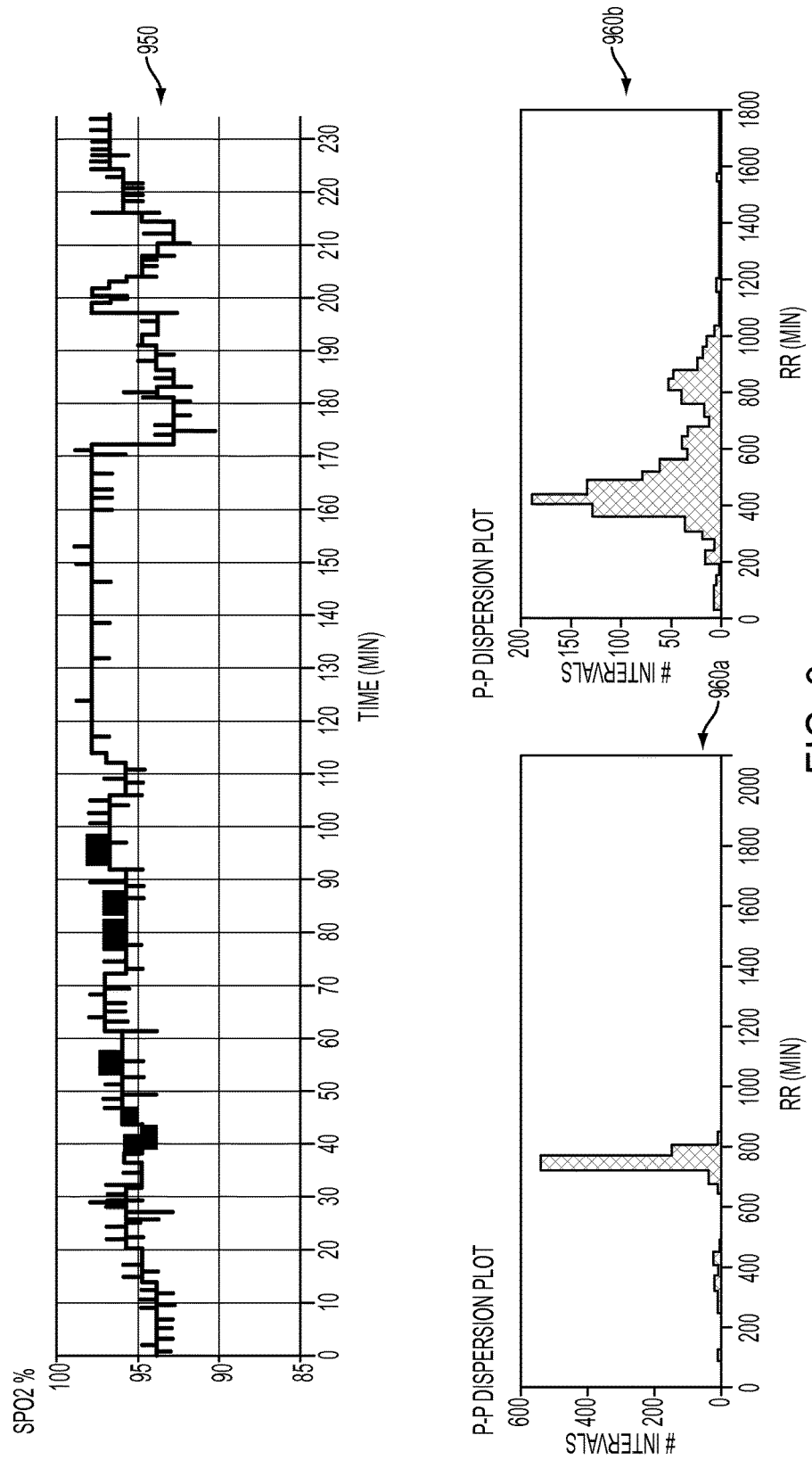
Figure 9:
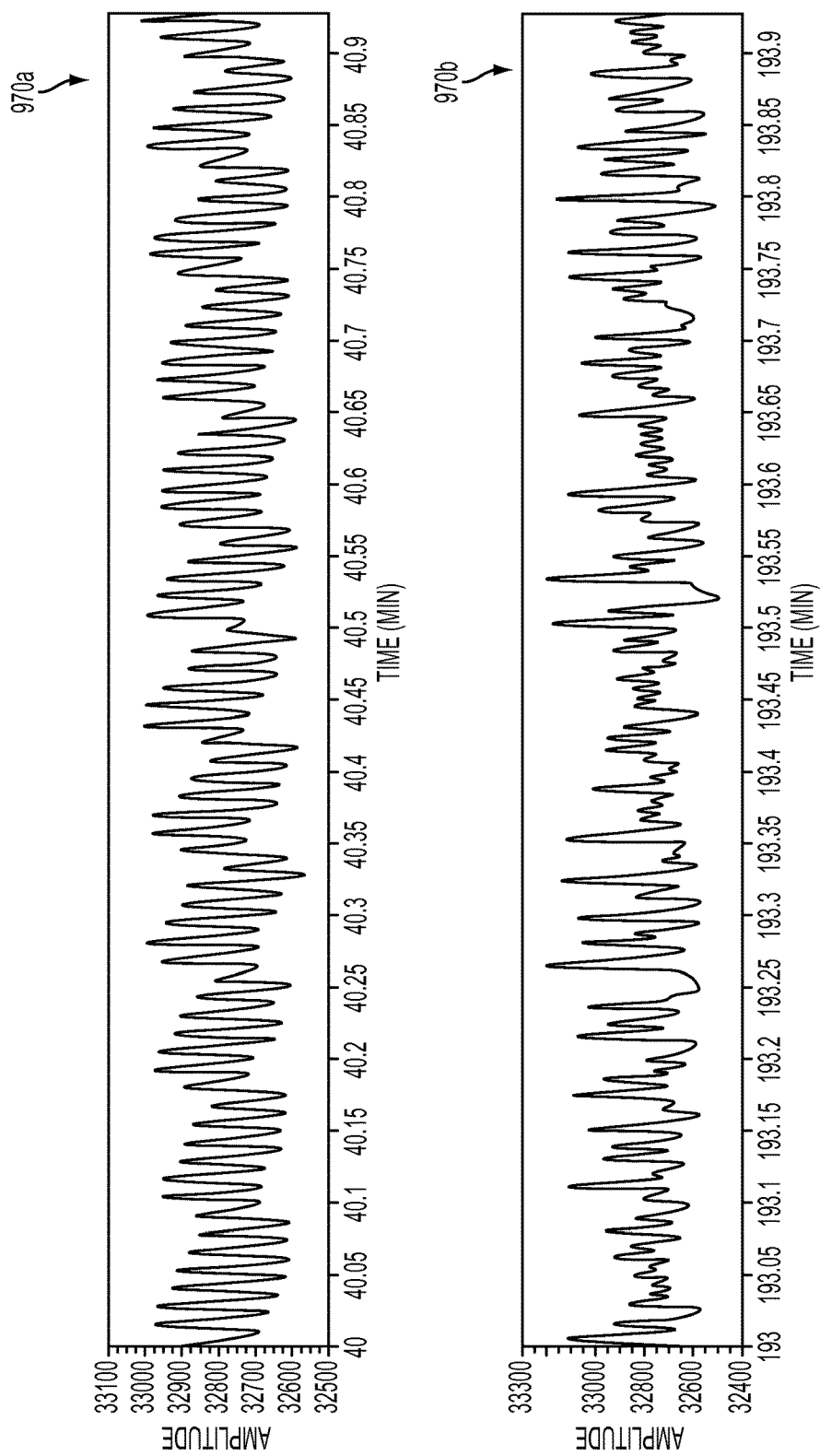

Example 3: An Annotated Output Display of Patient Data of a Patient Undergoing Dialysis Therapy It may be understood that an output display may include additional annotations including, but not limited to, date and time, patient identification information, patient diagnosis information, warning indicators, arrhythmia grading indicators, and data associated with a therapeutic device if the patient is undergoing a therapeutic procedure during pulse wave monitoring. FIG. 9 illustrates a non-limiting example of a computing device real-time output display to indicate the status of a patient undergoing dialysis. Exemplary data presented on such a display may include patient blood pressure 910, percent changes in patient pulse rate 930, percent changes in pulse strength 940, and patient blood oxygen saturation levels 950.

An indicator regarding patient status, such as a warning indicator 920, may also be provided to a user of the computing device. The warning indicator 920 may be triggered if any data associated with patient status, including data associated with pulse waveform peak amplitude differences, pulse waveform peak time differences, and one or more time difference dispersion metrics meet one or more warning criteria. Such warning criteria may be based, for example, on one or more arrhythmia grading systems. Exemplary arrhythmia grading systems may include the Lown grading system, the Bigger grading system, the Morganroth grading system, or any combination thereof. The warning criteria may be used by the health care provider as an indicator of patient hemodynamic instability or the potential onset of such instability. The health care provider may then assess the usefulness of continuing the therapeutic procedure or stopping it depending on the hemodynamic instability risk of the procedure to the patient.

Additional metrics associated with patient status, such as metrics associated with patient ventilation and patient blood chemistry (for example, additional blood gas metrics), may also be displayed. In one non-limiting example, such displays may be presented in real time by scrolling the data presented on the display.

Such a patient status display may also permit a health care provider and system user to display selected data presented during defined time windows. Such time windows may include an entire therapeutic session, a portion of a therapeutic session, or a time window including pre-therapy time, therapy time, and post therapy time. Thus, such a display window may display data generally over any time interval, including, without limitation, a time window for intervals of about 1 minute to about 24 hours. Non-limiting examples of such time window intervals may include time intervals of about 1 minute, about 2 minutes, about 5 minutes, about 10 minutes, about 20 minutes, about 30 minutes, about 1 hour, about 2 hours, about 5 hours, about 10 hours, about 20 hours, about 24 hours, and ranges between any two of these values including endpoints.

For example, in FIG. 9, anomalous changes in pulse rate 930 may be observed during the dialysis session between about 100 minutes and about 200 minutes of the dialysis procedure. Such changes may indicate a pre-pathological or pathological change in patient status as a result of a therapeutic procedure, such as due to hypovolemia during dialysis. It is noted that warning events are displayed in the alarm indicator 920 trace during this same time period. A health care provider may wish to obtain further information regarding the patient's status during this time window, especially with respect to baseline patient status. Thus, the health care professional may wish to observe the pulse volume waveform during a period of patient normative (that is, typical or non-pathological) cardiovascular behavior 970a and the pulse volume waveform during a period of patient anomalous cardiovascular behavior 970b to better characterize the anomaly.

As exemplified in FIG. 9, a pulse volume waveform trace may be displayed for a 1 minute window starting at time point 40 during a period of patient normative cardiovascular behavior 970a. An additional pulse volume waveform trace may be displayed for a 1 minute window starting at time point 193 during a period of patient anomalous cardiovascular behavior 970b. Both normative and anomalous pulse volume waveforms may be analyzed for metrics distinguishing the anomalous behavior from the normative behavior. One non-limiting method to analyze the pulse volume waveforms may include a dispersion analysis of the pulse volume peak occurrence time differences. A non-limiting example of such a dispersion analysis may include a histogram over a time window of differences in pulse volume occurrence times. A non-limiting example of a histogram of differences in pulse volume occurrence times during a period of normative cardiovascular behavior 960a may show normative features such as a narrow symmetrical peak at the reciprocal of the patient heart rate. Alternatively, a non-limiting example of a histogram of differences in pulse volume occurrence times during a period of anomalous cardiovascular behavior 960b may show anomalous features such as asymmetric peaks, well resolved multiple peaks, and center difference time values outside the normative patient values.

It may be understood that a user may control the display of patient status information provided by the computing device, such as a display of status data, types of data analysis results, and annotations of data analysis results. In one non-limiting example, a drop-down menu may be used by a user to indicate which types of information, analyses, and annotations may be displayed.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated in this disclosure, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can, of course, vary. It is also to be understood that the terminology used in this disclosure is for the purpose of describing particular embodiments only, and is not intended to be limiting.

With respect to the use of substantially any plural and/or singular terms in this disclosure, those having skill in the art can translate from the plural to the singular and/or from the singular to the plural as is appropriate to the context and/or application. The various singular/plural permutations may be expressly set forth in this disclosure for sake of clarity.

It will be understood by those within the art that, in general, terms used in this disclosure, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed in this disclosure also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed in this disclosure can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member.

From the foregoing, it will be appreciated that various embodiments of the present disclosure have been described for purposes of illustration, and that various modifications may be made without departing from the scope and spirit of the present disclosure. Accordingly, the various embodiments disclosed are not intended to be limiting, with the true scope and spirit being indicated by the following claims.

What is claimed is:

1. A method for identifying a cardiac dysrhythmia condition, the method comprising:
    receiving, by a computing device, a biological signal emulating an arterial pulse wave from a sensor in data communication with a human body;
    identifying, by the computing device, a plurality of signal peaks within the biological signal;
    identifying, by the computing device, a peak amplitude for each of the plurality of signal peaks;
    identifying, by the computing device, a time occurrence for each of the plurality of signal peaks;
    calculating, by the computing device, a plurality of amplitude differences, wherein each amplitude difference of the plurality of amplitude differences is calculated from a first peak amplitude of a first peak and a second peak amplitude of a second peak;
    calculating, by the computing device, a plurality of time differences, wherein each time difference of the plurality of time differences is calculated from a first time occurrence of the first peak and a second time occurrence of the second peak;
    composing, with the computing device, a histogram reflective of at least the plurality of time differences, the histogram including at least one peak around a primary time difference of the plurality of time differences;
    comparing, with the computing device, a plurality of amplitude differences with an amplitude threshold and a plurality of time differences with a time threshold to find at least one an anomalous amplitude difference that exceeds an amplitude threshold and at least one anomalous time difference that exceeds a time threshold;
    determining at least one time difference dispersion metric associated with the time difference histogram, the time difference dispersion metric including at least one of a peak width of the primary time difference peak, a secondary time difference peak in addition to the primary time difference peak, or an asymmetric primary time difference peak; and
    identifying a cardiac dysrhythmia condition based upon at least one of the time difference dispersion metrics associated with the time difference histogram during the occurrence of the at least one anomalous amplitude difference and the at least one anomalous time difference.

2. The method of claim 1, wherein the sensor is a pulse volume detection sensor.

3. The method of claim 1, wherein the sensor is one or more of a plethysmograph, a transmittance photo-optic sensor, a reflective photo-optic sensor, a pressure transducer, a tonometry device, a strain gauge, an ultrasound device, an electrical impedance measurement device, and a radar device.

4. The method of claim 1, wherein the sensor is a photoplethysmograph.

5. The method of claim 1, wherein identifying a plurality of signal peaks comprises fitting at least a portion of the biological signal to a mathematical model.

6. The method of claim 1, wherein the second peak amplitude is the peak amplitude occurring immediately after the first peak amplitude.

7. The method of claim 1, wherein the second time occurrence is the time occurrence occurring immediately after the first time occurrence.

8. The method of claim 1, further comprising calculating, by the computing device, the amplitude threshold.

9. The method of claim 8, wherein calculating the amplitude threshold comprises:
    calculating, by the computing device, an amplitude difference baseline from at least a portion of peak amplitude differences occurring within a data window; and
    adding, by the computing device, an amplitude difference offset to the amplitude difference baseline to yield the amplitude threshold.

10. The method of claim 9, wherein calculating the amplitude difference baseline comprises calculating, by the computing device, an average of peak amplitude differences of at least a portion of peak amplitude differences occurring within the data window.

11. The method of claim 9, wherein calculating the amplitude difference baseline comprises calculating, by the computing device, a maximum peak amplitude difference of at least a portion of peak amplitude differences occurring within the data window.

12. The method of claim 9, wherein the amplitude difference offset is calculated from an average of peak amplitude differences.

13. The method of claim 9, wherein the amplitude threshold equals about 1.05 to about 1.5 times the amplitude difference baseline.

14. The method of claim 9, wherein the amplitude threshold equals about 1.2 times the amplitude difference baseline.

15. The method of claim 1, further comprising calculating, by the computing device, the time threshold.

16. The method of claim 15, wherein calculating the time threshold comprises:
calculating, by the computing device, a peak time difference baseline from at least a portion of peak time differences occurring within a data window; and
adding, by the computing device, a peak time difference offset to the peak time difference baseline to yield the time threshold.

17. The method of claim 16, wherein calculating the peak time difference baseline comprises calculating, by the computing device, an average of a reciprocal of a normative pulse rate derived from the human body.

18. The method of claim 16, wherein the peak time difference offset is calculated from the peak time difference baseline.

19. The method of claim 16, wherein the time threshold equals about 1.05 to about 1.5 times the peak time difference baseline.

20. The method of claim 16, wherein the time threshold equals about 1.2 times the peak time difference baseline.

21. The method of claim 1, wherein the portion of the plurality of time differences occur within a data window.

22. The method of claim 21, wherein the data window has a window time of about 5 minutes to about 24 hours.

23. The method of claim 1, wherein the at least one time difference dispersion metric further includes one or more of a maximum value of at least one histogram peak, a value of a width metric of the at least one histogram peak, and a histogram primary time difference corresponding to the maximum value of the at least one histogram peak.

24. The method of claim 1, wherein identifying a type of cardiac dysrhythmia condition comprises classifying a type of cardiac dysrhythmia condition according to an arrhythmia grading system.

25. The method of claim 24, wherein the arrhythmia grading system comprises one or more of a Lown grading system, a Bigger grading system, a Morganroth grading system, or a combination thereof.

26. The method of claim 1, further comprising displaying, by the computing device on an output device, a representation of a portion of the biological signal along with at least one annotation identifying the cardiac dysrhythmia condition.

27. The method of claim 26, wherein displaying the representation of the portion of the biological signal comprises updating the representation of the portion of the biological signal over time.

28. The method of claim 26, wherein the annotation is an arrhythmia indicator.

29. The method of claim 26, wherein the annotation is an indicator of one or more criteria from a Lown grading system, a Bigger grading system, a Morganroth grading system, or a combination thereof.

30. The method of claim 1, further comprising issuing, by the computing device, a warning to a user if the cardiac dysrhythmia condition indicates an emergent condition associated with the human body.

* * * * *